US008216299B2

(12) United States Patent
Paul, Jr. et al.

(10) Patent No.: US 8,216,299 B2
(45) Date of Patent: Jul. 10, 2012

(54) METHOD TO RETRACT A BODY VESSEL WALL WITH REMODELABLE MATERIAL (75) Inventors: Ram H. Paul, Jr., Bloomington, IN (US); Brian C. Case, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 11/095,209

(22) Filed: Mar. 31, 2005

(65) Prior Publication Data
US 2005/0222661 A1 Oct. 6, 2005

Related U.S. Application Data (60) Provisional application No. 60/558,825, filed on Apr. 1, 2004.

(51) Int. Cl.
*A61F 2/06* (2006.01)
(52) U.S. Cl. ............... 623/1.38; 623/1.1; 623/23.75
(58) Field of Classification Search ............... 623/23.71, 623/23.75, 23.69, 23.7, 1.15, 1.38, 1.22, 623/1.49, 1.44, 1.51, 1.53, 1.1, 1.24, 1.41, 623/2.36, 2.38, 23.72; 606/200, 191, 194, 606/198, 192
See application file for complete search history.

(56) References Cited

U.S. PATENT DOCUMENTS

| | | |
|---|---|---|
| 3,589,392 A | 6/1971 | Meyer |
| 3,714,671 A | 2/1973 | Edwards et al. |
| 3,755,823 A | 9/1973 | Hancock |
| 3,903,548 A | 9/1975 | Nakib |
| 4,106,129 A | 8/1978 | Carpentier et al. |
| 4,178,638 A | 12/1979 | Meyer |
| 4,218,782 A | 8/1980 | Rygg |
| 4,222,126 A | 9/1980 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,470,157 A | 9/1984 | Love |
| 4,488,318 A | 12/1984 | Kaster |
| 4,580,568 A | 4/1986 | Gianturco |
| 4,605,407 A | 8/1986 | Black et al. |
| 4,643,732 A | 2/1987 | Pietsch et al. |
| 4,655,771 A | 4/1987 | Wallsten |
| 4,665,906 A | 5/1987 | Jervis |

(Continued)

FOREIGN PATENT DOCUMENTS
WO    WO 98/22158 A2    5/1998
(Continued)

OTHER PUBLICATIONS

Stephen Badylak, Ph.D., Klod Kokini, Ph.D., Bob Tullius, M.S., Abby Simmons-Byrd, R.V.T., Robert Morff, Ph.D., "Morphologic Study of Small Intestinal Submucosa as a Body Wall Repair Device," *Journal of Surgical Research*, 103, 190-202 (2002).

(Continued)

*Primary Examiner* — William H. Matthews
*Assistant Examiner* — Suba Ganesan
(74) *Attorney, Agent, or Firm* — Woodard, Emhardt, Moriarty, McNett & Henry LLP (57) ABSTRACT

The present invention provides remodelable materials for retracting the interior walls of a body vessel via remodeling processes. Also provided are methods, kits and devices for the same.

20 Claims, 4 Drawing Sheets

U.S. PATENT DOCUMENTS

| | | |
|---|---|---|
| 4,692,164 A | 9/1987 | Dzemeshkevich et al. |
| 4,725,274 A | 2/1988 | Lane et al. |
| 4,728,328 A | 3/1988 | Hughes et al. |
| 4,731,074 A | 3/1988 | Rousseau et al. |
| 4,732,152 A | 3/1988 | Wallstén et al. |
| 4,733,665 A | 3/1988 | Palmaz |
| 4,759,759 A | 7/1988 | Walker et al. |
| 4,778,461 A | 10/1988 | Pietsch et al. |
| 4,806,595 A | 2/1989 | Noishiki et al. |
| 4,848,343 A | 7/1989 | Wallstén et al. |
| 4,851,000 A | 7/1989 | Gupta |
| 4,863,467 A | 9/1989 | Bokros |
| 4,875,480 A | 10/1989 | Imbert |
| 4,902,508 A | 2/1990 | Badylak et al. |
| 4,904,254 A | 2/1990 | Lane |
| 4,935,030 A | 6/1990 | Alonso |
| 4,950,483 A | 8/1990 | Ksander et al. |
| 4,956,178 A | 9/1990 | Badylak et al. |
| 5,024,841 A | 6/1991 | Chu et al. |
| 5,026,377 A | 6/1991 | Burton et al. |
| 5,032,128 A | 7/1991 | Alonso |
| 5,035,706 A | 7/1991 | Giantureo et al. |
| 5,064,435 A | 11/1991 | Porter |
| 5,071,407 A | 12/1991 | Termin et al. |
| 5,078,720 A | 1/1992 | Burton et al. |
| 5,080,670 A | 1/1992 | Imamura et al. |
| 5,110,064 A | 5/1992 | Kimura et al. |
| 5,147,389 A | 9/1992 | Lane |
| 5,151,105 A | 9/1992 | Kwan-Gett |
| 5,163,951 A | 11/1992 | Pinchuk et al. |
| 5,211,649 A | 5/1993 | Kohler et al. |
| 5,256,418 A * | 10/1993 | Kemp et al. .................. 424/423 |
| 5,275,826 A | 1/1994 | Badylak et al. |
| 5,281,422 A | 1/1994 | Badylak et al. |
| 5,358,518 A | 10/1994 | Camilli |
| 5,366,473 A | 11/1994 | Winston et al. |
| 5,370,685 A | 12/1994 | Stevens |
| 5,375,612 A | 12/1994 | Cottenceau et al. |
| 5,376,112 A | 12/1994 | Duran |
| 5,376,113 A | 12/1994 | Jansen et al. |
| 5,397,351 A | 3/1995 | Pavcnik et al. |
| 5,411,552 A | 5/1995 | Andersen et al. |
| 5,413,599 A | 5/1995 | Imachi et al. |
| 5,423,887 A | 6/1995 | Love et al. |
| 5,449,384 A | 9/1995 | Johnson |
| 5,469,868 A | 11/1995 | Reger |
| 5,476,471 A | 12/1995 | Shifrin et al. |
| 5,489,298 A | 2/1996 | Love et al. |
| 5,500,014 A | 3/1996 | Quijano et al. |
| 5,509,930 A | 4/1996 | Love |
| 5,545,214 A | 8/1996 | Stevens |
| 5,591,195 A | 1/1997 | Taheri et al. |
| 5,607,465 A | 3/1997 | Camilli |
| 5,609,598 A | 3/1997 | Laufer et al. |
| 5,609,626 A | 3/1997 | Quijano et al. |
| 5,649,959 A | 7/1997 | Hannam et al. |
| 5,668,288 A | 9/1997 | Storey et al. |
| 5,683,448 A | 11/1997 | Cragg |
| 5,693,085 A * | 12/1997 | Buirge et al. ................ 623/1.13 |
| 5,711,969 A | 1/1998 | Patel et al. |
| 5,713,950 A * | 2/1998 | Cox ............................ 623/2.11 |
| 5,713,953 A | 2/1998 | Vallana et al. |
| 5,730,136 A | 3/1998 | Laufer et al. |
| 5,733,325 A | 3/1998 | Robinson et al. |
| 5,733,337 A | 3/1998 | Carr, Jr. et al. |
| 5,746,766 A | 5/1998 | Edoga |
| 5,755,782 A | 5/1998 | Love et al. |
| 5,769,780 A | 6/1998 | Hata et al. |
| 5,792,155 A | 8/1998 | Van Cleef et al. |
| 5,800,408 A | 9/1998 | Strauss et al. |
| 5,800,522 A | 9/1998 | Campbell et al. |
| 5,810,847 A | 9/1998 | Laufer et al. |
| 5,824,042 A | 10/1998 | Lombardi et al. |
| 5,824,043 A | 10/1998 | Cottone, Jr. |
| 5,824,054 A | 10/1998 | Khosravi et al. |
| 5,824,061 A | 10/1998 | Quijano et al. |
| 5,840,081 A | 11/1998 | Andersen et al. |
| 5,843,167 A | 12/1998 | Dwyer et al. |
| 5,843,171 A | 12/1998 | Campbell et al. |
| 5,851,232 A | 12/1998 | Lois |
| 5,855,597 A | 1/1999 | Jayaraman |
| 5,855,601 A | 1/1999 | Bessler et al. |
| 5,868,768 A | 2/1999 | Wicherski et al. |
| 5,879,382 A | 3/1999 | Boneau |
| 5,885,619 A | 3/1999 | Patel et al. |
| 5,891,193 A | 4/1999 | Robinson et al. |
| 5,895,419 A | 4/1999 | Tweden et al. |
| 5,902,334 A | 5/1999 | Dwyer et al. |
| 5,925,063 A | 7/1999 | Khosravi |
| 5,935,161 A | 8/1999 | Robinson et al. |
| 5,954,766 A | 9/1999 | Zadno-Azizi et al. |
| 5,955,110 A | 9/1999 | Patel et al. |
| 5,957,949 A | 9/1999 | Leonhardt et al. |
| 5,961,546 A | 10/1999 | Robinson et al. |
| 5,968,096 A | 10/1999 | Whitson et al. |
| 5,980,565 A | 11/1999 | Jayaraman |
| 5,993,844 A | 11/1999 | Abraham et al. |
| 5,997,573 A | 12/1999 | Quijano et al. |
| 6,004,347 A | 12/1999 | McNamara et al. |
| 6,015,431 A | 1/2000 | Thornton et al. |
| 6,022,374 A | 2/2000 | Imran |
| 6,033,398 A | 3/2000 | Farley et al. |
| 6,036,687 A | 3/2000 | Laufer et al. |
| 6,110,201 A | 8/2000 | Quijano et al. |
| 6,110,212 A | 8/2000 | Gregory |
| 6,117,979 A | 9/2000 | Hendriks et al. |
| 6,126,686 A | 10/2000 | Badylak et al. |
| 6,136,025 A | 10/2000 | Barbut et al. |
| 6,139,575 A | 10/2000 | Shu et al. |
| 6,143,022 A | 11/2000 | Shull et al. |
| 6,149,660 A | 11/2000 | Laufer et al. |
| 6,162,245 A | 12/2000 | Jayaraman |
| 6,168,614 B1 | 1/2001 | Andersen et al. |
| 6,176,875 B1 | 1/2001 | Lenker et al. |
| 6,187,036 B1 | 2/2001 | Shaolian et al. |
| 6,200,336 B1 | 3/2001 | Pavcnik et al. |
| 6,221,091 B1 | 4/2001 | Khosravi |
| 6,231,507 B1 | 5/2001 | Zikorus et al. |
| 6,241,763 B1 | 6/2001 | Drasler et al. |
| 6,245,102 B1 | 6/2001 | Jayaraman |
| 6,254,564 B1 | 7/2001 | Wilk et al. |
| 6,269,819 B1 | 8/2001 | Oz et al. |
| 6,280,467 B1 | 8/2001 | Leonhardt |
| 6,287,334 B1 | 9/2001 | Moll et al. |
| 6,287,335 B1 | 9/2001 | Drasler et al. |
| 6,287,339 B1 | 9/2001 | Vazquez et al. |
| 6,290,721 B1 | 9/2001 | Heath |
| 6,293,968 B1 | 9/2001 | Taheri |
| 6,296,661 B1 | 10/2001 | Davila et al. |
| 6,299,636 B1 | 10/2001 | Schmitt et al. |
| 6,299,637 B1 | 10/2001 | Shaolian et al. |
| 6,315,791 B1 | 11/2001 | Gingras et al. |
| 6,315,793 B1 | 11/2001 | Bokros et al. |
| 6,334,868 B1 | 1/2002 | Ham |
| 6,334,872 B1 | 1/2002 | Termin et al. |
| 6,334,873 B1 | 1/2002 | Lane et al. |
| 6,342,070 B1 | 1/2002 | Nguyen-Thien-Nhon et al. |
| 6,344,052 B1 | 2/2002 | Greenan et al. |
| 6,361,496 B1 | 3/2002 | Zikorus et al. |
| 6,379,710 B1 | 4/2002 | Badylak |
| 6,425,916 B1 | 7/2002 | Garrison et al. |
| 6,440,164 B1 | 8/2002 | DiMatteo et al. |
| 6,444,229 B2 | 9/2002 | Voytik-Harbin et al. |
| 6,451,051 B2 | 9/2002 | Drasler et al. |
| 6,454,799 B1 | 9/2002 | Schreck |
| 6,458,153 B1 | 10/2002 | Bailey et al. |
| 6,478,819 B2 | 11/2002 | Moe |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,562,068 B2 | 5/2003 | Drasler et al. |
| 6,562,069 B2 | 5/2003 | Cai et al. |
| 6,572,650 B1 | 6/2003 | Abraham et al. |
| 6,575,971 B2 | 6/2003 | Hauck et al. |
| 6,579,538 B1 | 6/2003 | Spievack |
| 6,582,462 B1 | 6/2003 | Andersen et al. |

| | | |
|---|---|---|
| 6,585,761 B2 | 7/2003 | Taheri |
| 6,602,286 B1 | 8/2003 | Strecker |
| 6,605,112 B1 | 8/2003 | Moll et al. |
| 6,632,243 B1 | 10/2003 | Zadno-Azizi et al. |
| 6,652,578 B2 | 11/2003 | Bailey et al. |
| 6,666,886 B1 | 12/2003 | Tranquillo et al. |
| 6,676,698 B2 | 1/2004 | McGuckin, Jr. et al. |
| 6,685,739 B2 | 2/2004 | DiMatteo et al. |
| 6,689,161 B2 | 2/2004 | Chen et al. |
| 6,695,833 B1 | 2/2004 | Frantzen |
| 6,695,878 B2 | 2/2004 | McGuckin, Jr. et al. |
| 6,705,585 B1 | 3/2004 | Roy |
| 6,716,241 B2 | 4/2004 | Wilder et al. |
| 6,730,118 B2 | 5/2004 | Spenser et al. |
| 6,752,828 B2 | 6/2004 | Thornton |
| 6,764,510 B2 | 7/2004 | Vidlund et al. |
| 6,830,585 B1 | 12/2004 | Artof et al. |
| 6,840,957 B2 | 1/2005 | DiMatteo et al. |
| 6,875,231 B2 | 4/2005 | Anduiza et al. |
| 7,159,593 B2 * | 1/2007 | McCarthy et al. ............ 128/898 |
| 2001/0005787 A1 | 6/2001 | Oz et al. |
| 2001/0007956 A1 | 7/2001 | Letac et al. |
| 2001/0010017 A1 | 7/2001 | Letac et al. |
| 2001/0011187 A1 | 8/2001 | Pavcnik et al. |
| 2001/0011189 A1 | 8/2001 | Drasler et al. |
| 2001/0021872 A1 | 9/2001 | Bailey et al. |
| 2001/0039450 A1 | 11/2001 | Pavcnik et al. |
| 2001/0044654 A1 | 11/2001 | Chen et al. |
| 2001/0047198 A1 | 11/2001 | Drasler et al. |
| 2002/0002401 A1 | 1/2002 | McGuckin et al. |
| 2002/0032481 A1 | 3/2002 | Gabbay |
| 2002/0055772 A1 | 5/2002 | McGuckin et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0107565 A1 | 8/2002 | Greenhalgh |
| 2002/0123800 A1 | 9/2002 | Taheri |
| 2002/0138135 A1 | 9/2002 | Duerig et al. |
| 2002/0151968 A1 * | 10/2002 | Zilla et al. .................... 623/1.39 |
| 2002/0151970 A1 | 10/2002 | Garrison et al. |
| 2002/0177894 A1 | 11/2002 | Acosta et al. |
| 2002/0188348 A1 | 12/2002 | DiMatteo et al. |
| 2003/0018358 A1 | 1/2003 | Saadat |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0051735 A1 | 3/2003 | Pavcnik et al. |
| 2003/0055492 A1 | 3/2003 | Shaolian et al. |
| 2003/0055495 A1 | 3/2003 | Pease et al. |
| 2003/0055496 A1 | 3/2003 | Cai et al. |
| 2003/0060875 A1 | 3/2003 | Wittens |
| 2003/0083741 A1 | 5/2003 | Woo et al. |
| 2003/0093071 A1 | 5/2003 | Hauck et al. |
| 2003/0114913 A1 | 6/2003 | Spenser et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0149477 A1 | 8/2003 | Gabbay |
| 2003/0171802 A1 | 9/2003 | Wilder et al. |
| 2003/0171824 A1 | 9/2003 | Abraham et al. |
| 2003/0175410 A1 | 9/2003 | Campbell et al. |
| 2003/0191525 A1 | 10/2003 | Thornton |
| 2003/0191528 A1 | 10/2003 | Quijano et al. |
| 2003/0195618 A1 | 10/2003 | Abraham et al. |
| 2003/0199971 A1 | 10/2003 | Tower et al. |
| 2003/0199972 A1 | 10/2003 | Zadno-Azizi et al. |
| 2003/0208261 A1 | 11/2003 | Thorpe et al. |
| 2003/0209835 A1 | 11/2003 | Chun et al. |
| 2003/0212452 A1 | 11/2003 | Zadno-Azizi et al. |
| 2003/0216764 A1 | 11/2003 | Tu et al. |
| 2003/0225447 A1 | 12/2003 | Majercak et al. |
| 2003/0229393 A1 | 12/2003 | Kutryk et al. |
| 2003/0236568 A1 | 12/2003 | Hojeibane et al. |
| 2004/0002719 A1 | 1/2004 | Oz et al. |
| 2004/0015230 A1 | 1/2004 | Moll et al. |
| 2004/0019374 A1 | 1/2004 | Hojeibane et al. |
| 2004/0024447 A1 | 2/2004 | Haverich |
| 2004/0024452 A1 | 2/2004 | Kruse et al. |
| 2004/0030249 A1 | 2/2004 | Willis |
| 2004/0034408 A1 | 2/2004 | Majercak et al. |
| 2004/0039436 A1 | 2/2004 | Spenser et al. |
| 2004/0049266 A1 | 3/2004 | Anduiza et al. |
| 2004/0054396 A1 | 3/2004 | Hartley et al. |
| 2004/0059411 A1 | 3/2004 | Strecker |
| 2004/0092858 A1 | 5/2004 | Wilson et al. |
| 2004/0093070 A1 | 5/2004 | Hojeibane et al. |
| 2004/0098098 A1 | 5/2004 | McGuckin et al. |
| 2004/0098112 A1 | 5/2004 | DiMatteo et al. |
| 2004/0106976 A1 | 6/2004 | Bailey et al. |
| 2004/0137618 A1 | 7/2004 | Chen et al. |
| 2004/0138684 A1 | 7/2004 | Eton |
| 2004/0167619 A1 | 8/2004 | Case et al. |
| 2004/0186558 A1 | 9/2004 | Pavcnik et al. |
| 2004/0193253 A1 | 9/2004 | Thorpe et al. |
| 2004/0199183 A1 | 10/2004 | Oz et al. |
| 2004/0210301 A1 | 10/2004 | Obermiller |
| 2004/0210306 A1 | 10/2004 | Quijano et al. |
| 2004/0210303 A1 | 10/2004 | Khairkhahan |
| 2004/0215339 A1 | 10/2004 | Drasler et al. |
| 2004/0225352 A1 | 11/2004 | Osborne et al. |
| 2004/0243222 A1 | 12/2004 | Osborne et al. |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2005/0027348 A1 | 2/2005 | Case et al. |
| 2005/0049692 A1 | 3/2005 | Numamoto et al. |
| 2005/0065594 A1 | 3/2005 | DiMatteo et al. |

FOREIGN PATENT DOCUMENTS

| | | |
|---|---|---|
| WO | WO 00/38590 A1 | 7/2000 |
| WO | WO 01/66161 A1 | 9/2001 |
| WO | WO 02/100245 A2 | 12/2002 |

OTHER PUBLICATIONS

Elias Brountzos, MD, Dusan Pavcnik, MD, PhD, Hans A. Timmermans, BFA, Christopher Corless, MD, PhD, Barry T. Uchida, BS, Edith S. Nihsen, BA, Manabu Nakata, MD, PhD, Maria Schoder, MD, John A. Kaufman, MD, Frederick S. Keller, MD, Josef Rösch, MD, "Remodeling of Suspended Small Intestinal Submucosa Venous Valve: An Experimental Study in Sheep to Assess the Host Cells' Origin," *J. Vasc. Interv. Radiol* vol. 14, No. 3, 349-356 (2003).

Zhonggang Feng, PhD., Toyoaki Matsumoto, Takao Nakamura, PhD., "Measurements of the mechanical properties of contracted collagen gels populated with rat fibroblasts or cardiomyocytes," *The Japanese Society for Artificial Organs*, 192-196 (2003).

Stephen S. Kim, Satoshi Kaihara, Mark S. Benvenuto, Byung-Soo Kim, David J. Mooney, Joseph P. Vacanti, "Small Intestinal Submucosa as a Small-Caliber Venous Graft: A Novel Model for Hepatocyte Transplantation on Synthetic Biodegradable Polymer Scaffolds with Direct Access to the Portal Venous System," *Journal of Pediatric Surgery*, Vo. 34, No. 1 124-128 (1999).

Fedor Lurie, MD, PhD, RVT, Robert L. Kistner, MD, Bo Eklof, MD, PhD, Darcy Kessler, RVT, "Mechanism of venous valve closure and role of the valve in circulation: A new concept," *Journal of Vascular Surgery*, vol. 38, No. 5, 955-961, (2003).

Jonathan A. Phillips, Charles A. Vacanti, Lawrence J. Bonassar, "Fibroblasts regulate contractile force independent of MMP activity in 3D-collagen," *Elsevier BBRC*, 312, 725-732 (2003).

R.A. Roeder, G.C. Lantz, DVM, L.A. Geddes, ME, PhD, FACC, FRSM, "Mechanical Remodeling of Small-Intestine Submucosa Small-Diameter Vascular Grafts—A Preliminary Report," *Biomedical Instrumentation & Technology*, 110-120 (2001).

G.E. Sandusky, Jr., S.F. Badylak, R.J. Morff, W.D. Johnson, G. Lantz, "Histologic Findings After In Vivo Placement of Small Intestine Submucosal Vascular Grafts and Saphenous Vein Grafts in the Carotid Artery in Dogs," *American Journal of Pathology*, vol. 140, No. 2, 317-324 (1992).

Ulrika Zagai, Karin Fredriksson, Stephen I. Rennard, Joachim Lundahl, C. Magnus Sköld, "Platelets stimulate fibroblast-mediated contraction of collagen gels," *Respiratory Research*, 4:13, (2003).

Janice M. Zaleskas, Bernd Kinner, Toby M. Freyman, Joannis V. Yannas, Lorna J. Gibson, Myron Spector, "Contractile forces generated by articular chondrocytes in collagen-glycosaminoglycan matrices," *Elsevier Biomaterials*, 25 1299-1308 (2004).

* cited by examiner

METHOD TO RETRACT A BODY VESSEL WALL WITH REMODELABLE MATERIAL

RELATED APPLICATIONS

This application claims benefit of U.S. Provisional Patent Application 60/558,825, filed Apr. 1, 2004, entitled "Method to Retract a Body Vessel Wall with Remodelable Material," which is incorporated herein by reference in its entirety.

TECHNICAL FIELD

The present disclosure relates to the implantation of remodelable material within a body vessel. Implantation of remodelable material can advantageously cause the retraction of the body vessel, and preferably improve the function of a valve or a sphincter within the body vessel.

BACKGROUND

Many vessels in animals transport fluids from one body location to another. Frequently, fluid flows in a substantially unidirectional manner along the length of the vessel. For example, veins in the body transport blood to the heart and arteries carry blood away from the heart.

It is often desirable to retract the wall of a body vessel to correct or mitigate undesirable medical conditions, such as correcting compromised function of sphincter muscles or valves within a body vessel. Certain medical conditions are ameliorated by restricting the caliber of portions of a body vessel, such as the esophagus, urethra, ureter, bile duct, or a vein. For example, restriction of a body vessel near a defective sphincter muscle may improve or restore sphincter function. Several undesirable medical conditions can result from the inability of sphincter muscles to close completely. Gastroesophageal reflux disease (GERD) involves a deficiency of the pyloric sphincter, leading to the regurgitation of stomach contents into the esophagus or diaphragm. Urinary incontinence and/or vesicoureteral reflux can result from malfunction of sphincter muscles surrounding the urethra or ureters. Retraction of portions of the esophagus, ureters, urethra, or other body vessels may advantageously improve sphincter function associated with these vessels.

Furthermore, restriction of a body vessel may improve the function of defective valves within the body vessel. In many body vessels, including mammalian veins, natural valves are positioned along the length of the vessel in the form of leaflets disposed annularly along the inside wall of the vein which open to permit blood flow towards the heart and close to restrict back flow. These natural venous valves open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflet structures, when functioning properly, extend radially inwardly toward one another such that the tips contact each other to restrict backflow of blood.

In the condition of venous valve insufficiency, the valve leaflets do not function properly. Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur in the superficial venous system, such as the saphenous veins in the leg, or in the deep venous system, such as the femoral and popliteal veins extending along the back of the knee to the groin.

Recently, various intraluminally implantable prosthetic devices and minimally invasive methods for intraluminal implantation of these devices have been developed. Such prosthetic venous valve devices can be inserted intravascularly, for example from an implantation catheter. Prosthetic devices can function, for example, as a replacement venous valve, or restore native venous valve function by bringing incompetent valve leaflets into closer proximity. However, vascular devices are typically not highly responsive to conditions within the body vessel, and typically do not provide for the gradual retraction of the vessel wall over a period of hours, days or weeks.

It is desirable to find improved ways to desirably retract a body vessel wall, for example to improve the function of incompetent sphincter muscles or incompetent valves within the vessel lumen. Preferably, the implantation of a remodelable material as described herein desirably retracts a portion of the body vessel wall in a manner responsive to conditions within the body vessel while gradually narrowing a portion of the body vessel wall.

SUMMARY

The present invention provides various methods, devices and kits for improving body function by retracting the walls of a body vessel. Preferably, implanting remodelable biological material in contact with an interior wall of a body vessel induces remodelable retraction of the body vessel wall. In one embodiment, the body vessel is a vein. In other embodiments, the body vessel comprises a sphincter muscle, such as an esophagus or urethra. Furthermore, the porosity of the remodelable material can be varied in some embodiments to permit diffusion of essential fluid components from the blood to the nearby tissue.

In one embodiment, the present invention provides methods for remodelably contracting the lumen of a body vessel by implanting a remodelable material in contact with the interior wall of the body vessel. Remodelable material can be implanted at any suitable location within a body vessel. For example, the venous valve can be an incompetent venous valve having impaired function. Remodelable retraction of one or more leaflet bases of a venous valve can beneficially draw the leaflets of an incompetent venous valve into greater proximity so as to improve or restore venous valve function. Examples of a venous valve include a native venous valve, a partially remodeled implanted venous valve comprising autologous tissue, or a prosthetic venous valve without autologous tissue.

The time for remodelable retraction to begin may vary. Remodeling may begin immediately after implantation, and remodelable retraction thereafter. For example, remodelable retraction may begin within moments, and is typically observable within a few hours to about two days. Once the process of remodelable retraction begins, the body vessel wall can be substantially retracted within about one year, preferably between about five days and six months, after implantation of the remodelable material.

A variety of remodelable materials can be used, including an extracellular matrix material like small intestine submucosa (SIS). The remodelable material can be formed in any suitable configuration, including tubular, zig-zag, helical, coil, horse-shoe, and ring configurations. The remodelable material may comprise one or more layers in any suitable configuration.

The remodelable material can be deployed from an intraluminal delivery device, such as a catheter-based delivery system. Preferably, the delivery system comprises a catheter operably connected to a remodelable material. In some embodiments, the delivery system can comprise a balloon at the proximal end of the catheter, a protective sheath and pusher assembly, or a self-expanding support frame. The delivery system can also comprise a retaining mechanism such as a clip or other retention mechanism for holding the remodelable material during the delivery procedure. In some embodiments, the delivery system can also provide for measurement of a distance within the body vessel lumen. For example, the delivery device can provide indicia or signals relating to the location or orientation of the remodelable material within the body vessel, or the distance traveled along a body vessel lumen.

The remodelably material is preferably adapted to be maintained in contact with a portion of the interior surface of a body vessel for a time sufficient to permit remodelable retraction of the body vessel wall to occur. For example, the remodelable material can be secured at a point of treatment using a variety of means, such as expansion of a support frame or inflation of a balloon. The remodelable material can, in one embodiment, be attached to a support frame, such as a bioabsorbable support frame. The remodelable material or support frame can be adapted to secure the remodelable material in the lumen of a body vessel. For example, barbs can be formed in either the remodelable material or the support frame, or both, to securably engage the interior wall of the body vessel. Also, the remodelable material can comprise perforations or holes to enhance adhesion to the interior wall of the body vessel. Multiple remodelable material implants can be deployed in some embodiments.

In some embodiments, the remodelable material is treated with a bioactive such as heparin, pentoxifylline (PTX) or a cross-linking agent. In one embodiment, the remodelable material comprises aligned collagen fibers. The remodelable material can also comprise multiple layers of the same or different remodelable material in one or more of the layers.

Also provided are methods of treating a subject exhibiting symptoms of venous valve related illnesses, as well as methods of treating subjects diagnosed as such. Remodelable material can be implanted upstream from or downstream from a venous valve, or both upstream to and downstream from a venous valve. A remodelable material can also be deployed in various body vessels to treat a variety of other conditions, including: gastroesophageal reflux disease, urinary and rectal incontinence, dysphonia, and the reconstruction of body vessels.

Another embodiment provides methods of treating venous valve insufficiency comprising the step of implanting remodelable material within the lumen of a body vessel near a venous valve. Devices comprising remodelable material for implantation within the lumen of a body vessel to remodelably retract the interior wall of the body vessel are also provided. In one embodiment, the device comprises a delivery device or system comprising a catheter that is operably connected to a remodelable material. The remodelable material, the delivery catheter, or the combination thereof, can be configured for deployment of the remodelable material within the lumen of the body vessel at a distance from the base of a leaflet of a venous valve.

The present invention is illustrated by the embodiments described herein, and further includes combinations of the embodiments as read by one of ordinary skill in the art.

DETAILED DESCRIPTION OF THE EMBODIMENTS

For the purposes of promoting an understanding of the principles of the invention, the following provides a detailed description of some embodiments of the invention as illustrated by the drawings. The description is not intended to limit the invention in any manner, but rather serves to enable those skilled in the art to make and use the invention. As used herein the terms "comprise(s)," "include(s)," "having," "has," "can," "contain(s)," and variants thereof, are intended to be open-ended transitional phrases, terms, or words that do not preclude the possibility of additional acts or structure. The present invention also contemplates other embodiments "comprising," "consisting of" and "consisting essentially of," the embodiments or elements presented herein, whether explicitly set forth or not.

An "upstream" direction within a vein is away from the heart; a "downstream" direction within a vein is toward the heart.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, the term "body vessel" means any body passage lumen, including but not limited to blood vessels such as those of the human vasculature system, billiary ducts, esophagus, urethra and ureteral passages.

As used herein, "endolumenally," "intraluminally" or "transluminal" all refer synonymously to implantation placement by procedures where the prosthesis is advanced within and through the lumen of a body vessel from a remote location to a target site within the body vessel. In vascular procedures, a medical device will typically be introduced "endovascularly" using a catheter over a guidewire under fluoroscopic guidance. The catheters and guidewires may be introduced through conventional access sites to the vascular system.

A "venous valve" can refer to a native venous valve congenitally formed within blood vessels, implanted artificial venous valves, as well as venous valves subsequently grown from remodeled tissue implanted within blood vessels. Native venous valve leaflets are typically thin sheets of collagen-containing tissue attached to the interior wall of a body vessel at a leaflet base.

Venous Valve Function and Venous Valve Incompetence

Figure 1:
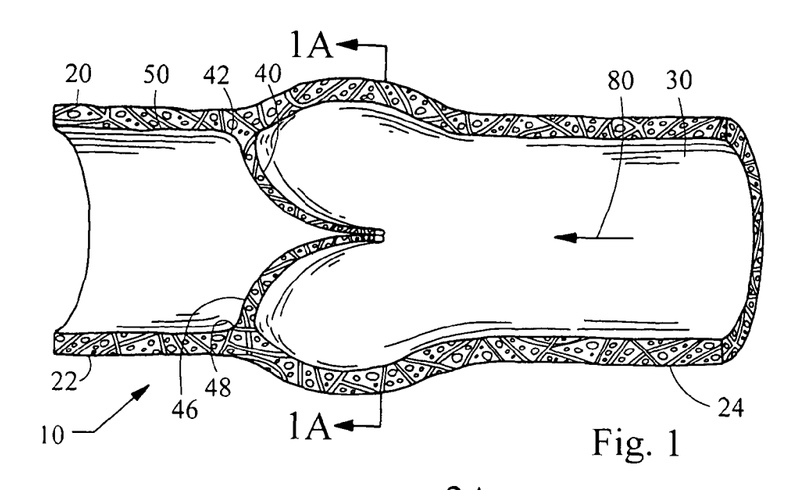
FIG. 1 and FIG. 2 provide cut-away views showing the operation of a competent venous valve and FIG. 1A and FIG. 2A provide cross-sectional view of same.
Figure 2:
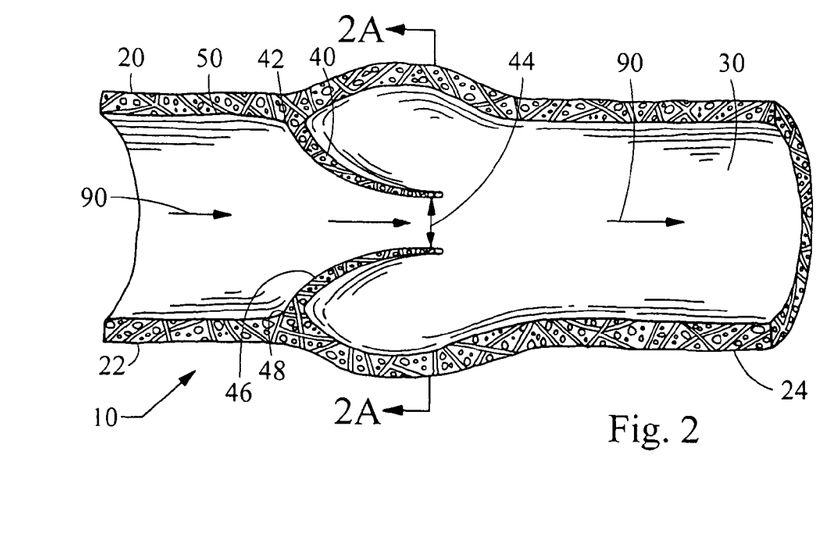

The anatomy and function of a competent venous valve is illustrated in FIG. 1 and FIG. 2. A venous valve 10 comprises a first leaflet 40 and a second leaflet 46 disposed opposite each other within the lumen 30 defined by the interior wall 50 of a body vessel 20.

The normal operation of a competent venous valve is illustrated in FIG. 1 and FIG. 2. The venous valve 10 permits fluid flow 90 toward the heart (downstream), while substantially preventing retrograde fluid flow 80 in the opposite (upstream) direction. As shown in FIG. 1 and FIG. 2, a first leaflet 40 is attached to the interior wall 50 of the body vessel 20 at a first leaflet base 42, and a second leaflet 46 is similarly attached at a second leaflet base 48. A "leaflet base" refers to the portion of a venous valve leaflet attaching the leaflet to a body vessel or support frame. Leaflet bases are typically semicircular interfaces where the leaflet material projects away from the interior wall 50 of the vessel lumen 30 toward the center of the lumen. During normal function, fluid flow 90 moves freely from an upstream end 22 of the venous valve 10, through the valve 10, toward the downstream end 24 of the vein, and substantially prevents retrograde flow 80 in an opposite (upstream) direction.

Figure 1A:
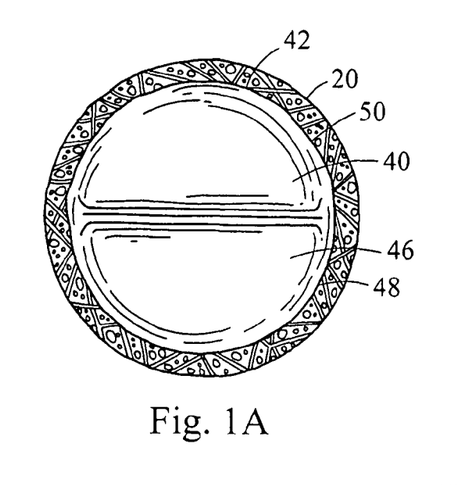
Figure 2A:
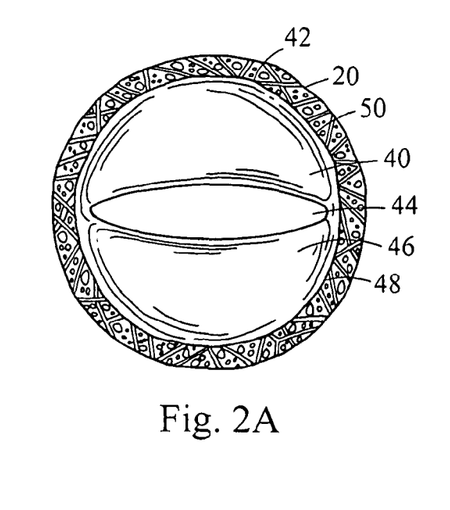

The cross-sectional area of the lumen 30 a body vessel can vary in size and shape when the body vessel is a vein. For example, the cross-sectional shape of a vein can vary from circular during periods of high fluid flow, to more elliptical during periods of lower rates of fluid flow. The shape of veins fluctuates in response to a variety of factors, including muscle pressure, cardiac cycle and breathing cycle. In FIG. 1 and FIG. 2, the body vessel 20 is a vein shown with a lumen 30 having a circular cross-section defined by the imaginary line 1A-1A in FIG. 1 and imaginary line 2A-2A in FIG. 2. FIG. 1A shows the cross-sectional view along line 1A-1A in FIG. 1 and FIG. 2A shows the cross-sectional view along line 2A-2A in FIG. 2. During fluid flow 90 through the valve 10, as shown in FIG. 2, the first leaflet 40 and the second leaflet 46 are pushed open by the pressure of the fluid, creating a substantially elliptical valve opening 44 through which the fluid flows through the body vessel lumen 30. When fluid flow 90 is not present, or fails to exert sufficient pressure to open the leaflets, the first leaflet 40 and the second leaflet 42, close together to substantially prevent retrograde flow 80 in the upstream direction.

Without being bound to the mechanisms of leaflet function disclosed therein, a recent study of venous valve leaflet function from Lurie et al. provides more details of one view in the art of the anatomy and operation of competent venous valves. Lurie et al., "Mechanisms of venous valve closure and role of the valve in circulation: A new concept," J. Vasc. Surg. 38(5): 955-61 (November 2003), hereby incorporated by reference in its entirety.

An "incompetent" venous valve, as recognized in the art, is a venous valve with impaired function. Any venous valve can become incompetent, including a prosthetic or native venous valve. Venous valve incompetence can occur in various ways. For example, in one mode of failure, the valve leaflets fail to extend sufficiently radially inward from the walls of a body vessel to contact each other and adequately restrict retrograde flow within the body vessel. Such a condition, found in subjects with venous valve insufficiency, can result from thickening, stiffening or retraction of the venous valve leaflets, or from dilation of the blood vessel. Retraction of the walls of a vessel can, in some embodiments, ameliorate venous valve incompetency and even restore venous valve function by drawing the leaflets of an incompetent venous valve closer together, for example by pulling the leaflets closer toward the center of the body vessel lumen.

Figure 3:
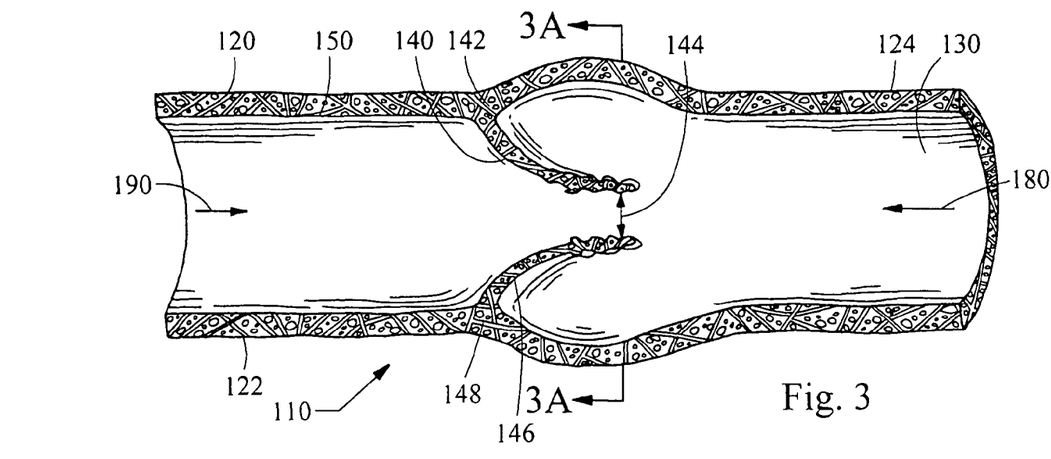
FIG. 3 provides a cut-away view of an incompetent venous valve and a cross-sectional view of same.
Figure 3A:
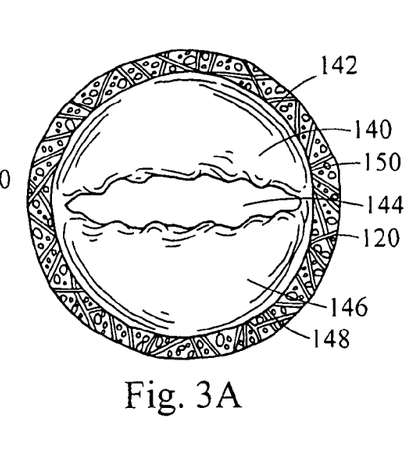

FIG. 3 illustrates an incompetent venous valve 110. FIG. 3A shows a cross-sectional view along imaginary line 3A-3A shown in FIG. 3. The venous valve 110 comprises two leaflets disposed within the lumen 130 of a body vessel 120. A first leaflet 140 is attached to the interior wall 150 of the body vessel 120 at a first leaflet base 142, and a second leaflet 146 is similarly attached at a second leaflet base 148. Leaflet bases are typically semi-circular interfaces where the leaflet material projects away from the interior wall 150 of the vessel lumen 130 toward the center of the lumen. The leaflets permit fluid flow 190 in a downstream direction. However, unlike a competent venous valve, the leaflets of the incompetent venous valve do not sufficiently coapt to prevent retrograde fluid flow 180 in the upstream direction. For example, an incompetent venous valve 110 may be characterized by a gap 144 between the leaflets during retrograde fluid flow 180. Accordingly, in some incompetent venous valves, fluid is permitted to flow in two directions instead of substantially in only one direction. Incompetency of venous valves, for instance as illustrated in FIG. 3, can lead to conditions such as chronic venous valve insufficiency.

Remodelable Materials

A "remodelable material," as further discussed below, is any material or combination of materials that can undergo biological processes of remodeling when placed in communication with a living tissue, such that the remodelable material is transformed into material that is substantially similar to said living tissue in cellular composition. Unless otherwise specified herein, a "remodelable material" includes a single layer material, or a multiple layers of one or more materials that together undergo remodeling when placed in communication with living tissue. Preferably, a remodelable material retracts upon contact for 90 days or less with living tissue of the type present at an intended site of implantation, such as the interior of a body vessel.

One example of a remodeling process is the migration of cells into the remodelable material. Migration of cells into the remodelable material can occur in various ways, including physical contact with living tissue, or recruitment of cells from tissue at a remote location that are carried in a fluid flow to the remodelable material. In some embodiments, the remodelable material can provide an acellular scaffold or matrix that can be populated by cells. The migration of cells into the remodelable material can impart new structure and function to the remodelable material. In some embodiments, the remodelable material itself can be absorbed by biological processes. In some embodiments, fully remodeled material can be transformed into the living tissue it is in contact with through cellular migration from the tissue into the remodelable material, or provide the structural framework for tissue. Non-limiting examples of remodelable materials, their preparation and use are also discussed herein.

Any remodelable material, or combination of remodelable materials, that retracts during remodeling can be used as a remodelable material for practicing the present invention. For instance, naturally derived or synthetic collagen can provide retractable remodelable materials. Naturally derived or synthetic collagenous material, such as extracellular matrix material, are suitable remodelable materials. Examples of remodelable materials include, for instance, submucosa, renal capsule membrane, dura mater, pericardium, serosa, and peritoneum or basement membrane materials. Collagen can be extracted from various structural tissues as is known in the art and reformed into sheets or tubes, or other shapes. The remodelable material may also be made of Type III or Type IV collagens or combinations thereof. U.S. Pat. Nos. 4,950,483, 5,110,064 and 5,024,841 relate to such remodelable collagen materials and are incorporated herein by reference. Further examples of materials useful as remodelable materials include: compositions comprising collagen matrix material, compositions comprising epithelial basement membranes as described in U.S. Pat. No. 6,579,538 to Spievack, the enzymatically digested submucosal gel matrix composition of U.S. Pat. No. 6,444,229 to Voytik-Harbin et al., materials comprising the carboxy-terminated polyester ionomers described in U.S. Pat. No. 5,668,288 to Storey et al., collagen-based matrix structure described in U.S. Pat. No. 6,334,872 to Termin et al., and combinations thereof.

In some embodiments, submucosal tissues for use as remodelable materials include intestinal submucosa, stomach submucosa, urinary bladder submucosa, and uterine submucosa. A specific example of a suitable remodelable material is intestinal submucosal tissue, and more particularly intestinal submucosa delaminated from both the tunica muscularis and at least the tunica mucosa of warm-blooded vertebrate intestine.

Submucosal tissue can be obtained from various tissue sources, harvested from animals raised for meat production, including, for example, pigs, cattle and sheep or other mammals. In general, submucosa is prepared from these tissue sources by delaminating the submucosa from both the smooth muscle layers and the mucosal layers. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting stomach submucosa tissue has a thickness of about 100 to about 200 micrometers, and consists primarily (greater than 98%) of acellular, eosinophilic staining (H&E stain) extracellular matrix material. The submucosal tissue graft constructs of the present invention can be prepared and sterilized using sterilization techniques known in the art, including those discussed in U.S. Pat. No. 6,126,686, as well as the references cited therein.

Submucosal tissue can be stored in a hydrated or dehydrated state. Lyophilized or air dried submucosa tissue can be rehydrated and used in accordance with this invention without significant loss of its biotropic and mechanical properties.

One specific type of remodelable materials is extracellular matrix material derived from submocosal tissue, called small intestine submucosa (SIS). SIS can be made, for example, in the fashion described in U.S. Pat. No. 4,902,508 to Badylak et al., U.S. Pat. No. 5,733,337 to Carr, and WIPO Patent No. WO 9822158, published May 28, 1998, issued to Cook Biotech Inc. et al. and listing Patel et al. as inventors. The preparation and use of SIS is also described in U.S. Pat. Nos. 5,281,422 and 5,275,826. The use of submucosal tissue in sheet form and fluidized forms for inducing the formation of endogenous tissues is described and claimed in U.S. Pat. Nos. 5,281,422 and 5,275,826, the disclosures of which are incorporated herein by reference. SIS is also described in detail in U.S. Pat. Nos. 4,956,178 and 5,281,422, all of which are incorporated herein by reference.

Without being bound to theory, preliminary biochemical analyses suggest that the composition of small intestinal submucosa is similar to that of other basement membrane/extracellular matrix structures, and consists of a complex array of collagens, proteoglycans, glycosaminoglycans, and glycoproteins. The major components commonly identified in extracellular matrix tissues similar to submucosal tissue include the cell adhesion proteins, fibronectin, vitronectin, thrombospondin, and laminin; the structural components, collagens and elastin; and the proteoglycans, serglycin, versican, decorin, and perlecan.

Upon implantation, remodelable materials, such as submucosal tissue, undergo remodeling and induce the growth of endogenous tissues upon implantation into a host.

Remodelable Retraction

The phrase "remodelably retract" refers to the process of retraction at least partly induced by the contraction of a remodelable material during the remodeling process. In some embodiments, remodelable retraction draws the interior wall of a body vessel, such as a vein, radially inward within the lumen of the body vessel. During the process of remodelable retraction, a portion of the interior wall of a body vessel can be drawn radially inward, reducing the volume of the body vessel lumen. In some embodiments, the inward retraction of the vessel wall begins about two days after implantation of the remodelable material. For example, the inward retraction could coincide with the onset of biological process of remodeling after implantation of the remodelable material. In some embodiments, the inward retraction can substantially occur within one year, preferably within six months.

Without being limited to theory, it is believed that one or more various biological processes may occur during remodelable retraction. For example, cell mediated contraction of a remodelable material after migration of cells into the remodelable material can induce retraction of other tissue in communication with the remodelable material. In one embodiment, remodelable material attached to the interior wall of a body lumen with barbs can remodelably retract the walls of the body lumen as the remodelable material undergoes remodeling.

Numerous studies have shown that remodelable material, such as submucosal tissue, is capable of inducing host tissue proliferation, remodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization are observed and the submucosa extracellular matrix material is remodeled into host replacement tissue with site-specific structural and functional properties.

Remodelable materials such as extracellular matrix materials can provide structural scaffolds into which cells from the host body can migrate and inhabit. Interactions between extracellular matrix components and cells can, in turn, mediate processes which are fundamental to migration, proliferation and differentiation during development. Without being limited to theory, it is believed that the ability of the matrix to bind molecules allows cells to secrete or sequester proteins, proteoglycans or other molecules, allowing cells to send chemical signals to surrounding cells. Cells could respond to these signals, for example, through adhesion, proliferation, migration, differentiation, metabolism or further secretion and sequestering of molecules. This is one type of mechanism by which cells can propagate the signal and possibly change the tissue properties in response to environmental change that initiated the chain of events during the remodeling process.

In addition to providing a destination for migration of various host body cells upon implantation within the body, remodelable materials often tend to contract during the remodeling process. When cells such as fibroblasts, chondrocytes, cardiomyocytes or others, migrate to and populate an implanted remodelable matrix material such as a collagen matrix, the cells can undergo a variety of changes when activated, including establishing a contractile mechanism. Without being limited to theory, some investigations have suggested that platelets and platelet lysates, such as platelet-derived growth factor (PDGF) and transforming growth factor-beta (TGF-beta), may partially mediate this activation of a contractile mechanism. The cellular contractile mechanism, also called cell-mediated contraction, has been shown to result in contraction of collagen gels in vitro and may play an active role in the remodeling of extracellular matrix and extracellular matrix contraction. Remodelable matrix materials, such as extracellular matrix material, can have a three-dimensional structure capable of translating mechanical strain of the tissue to the cells through cell attachment points called ligands, which link the cells to the matrix. "Mechanical strain" refers to strain caused by, resulting from, or relating to a process that involves a physical, as opposed to a chemical, change. The structure and consistency of the extracellular matrix material allow translation of contractile and tensile loads in multiple axes to the cells as the loads are imparted on the tissue.

Examples of recent studies of the contraction of remodelable matrix materials include: Feng Z, M. T. et al., "Measurements of the mechanical properties of contracted collagen gels populated with rat fibroblasts or cardiomyocytes." J. Artif Organs. 6(3): 192-6 (2003); Phillips J. A. et al., "Fibroblasts regulate contractile force independent of MMP activity in 3D-collagen." Biochem. Biophys. Res. Comm. 312(3): 725-32 (2003); Zagai U. et al., "Platelets stimulate fibroblast-mediated ontraction of collagen gels," Respir. Res. 4(1): 13 (2003); Zaleskas J. M. et al., "Contractile forces generated by articular chondrocytes in collagen-glycosaminoglycan matrices." Biomaterials 25(7-8): 1299-308 (2004). These references are incorporated by reference herein.

Treatment and Configurations of Remodelable Material

In some embodiments, the remodelable material can comprise processed tissue matrices that are treated or modified, either physically or chemically, prior to implantation of the remodelable material. Physical modifications such as shaping, conditioning by stretching and relaxing, or perforating the cleaned tissue matrices may be performed as well as chemical modifications such as binding growth factors, selected extracellular matrix components, genetic material, and other agents that would affect bioremodeling and repair of the body part being treated, repaired, or replaced.

The remodelable material can be prepared or treated in various ways to control or influence the effect of the remodelable material on the wall of the body vessel, including influencing the process of remodelable retraction. Various methods of preparing remodelable tissue known in the art can be used to prepare or treat the remodelable materials for implantation herein. For example, the remodelable material can be treated to control the amount and time of retraction during remodeling. U.S. Pat. Nos. 6,572,650 and 5,993,844 to Abraham et al., which are incorporated herein by reference, disclose such methods for preparation of remodelable materials for intraluminal implantation that influence the amount and time of retraction during remodeling.

A remodelable material can also comprise composites of material from different sources or one or more layers of materials derived from different sources, or materials treated or configured in different manners. Multiple layers of different materials layered to form a remodelable material effective to promote desirable properties within a body vessel, such as controlling the rate of remodeling. For example, a remodelable material can comprise ECM material derived from different sources (synthetic or naturally-occurring) that are joined together within a single layer or joined as separate layers. The first, second and third ECM materials can be independently derived from submucosa, renal capsule membrane, dura mater, pericardium, serosa, and peritoneum or basement membrane materials. A remodelable material may comprise one or more layers comprising ECM material oriented in multiple directions. Strips of remodelable material from the same or different sources can be woven together.

A remodelable material can be made thicker by making multilaminate constructs, for example SIS constructs as described in U.S. Pat. Nos. 5,968,096; 5,955,110; 5,885,619; and 5,711,969, incorporated herein by reference. In addition to xenogenic biomaterials, such as SIS, autologous tissue can be harvested and used in a remodelable material as well. Remodelable materials can comprise allographs such as harvested native tissue. Additionally, remodelable materials optionally comprise Elastin or Elastin-Like Polypetides (ELPs).

A remodelable material can comprise ECM material subjected to different chemical or physical treatments, or shaped differently. For example, a remodelable material can comprise a first layer that is a cross-linked layer of ECM material from a first source joined to a second layer that is a non-cross-linked layer of an ECM material from a second source that is joined to a third layer that is an ECM material from a third sour that comprises a bioactive coating. A remodelable material can also comprise elastin. A composite remodelable material comprises material derived from two or more sources or multiple layers of remodelable materials.

A remodelable material may also comprise a bio-compatible material such as Dacron, expanded polytetrafluoroethylene (ePTFE) or other synthetic bio-compatible material.

In one embodiment, the remodelable material comprises at least two ECM materials derived from different sources in the same layer, or in different layers. In another embodiment, the remodelable material comprises an ECM material and an elastin material. In yet another embodiment, the remodelable material is a woven material comprising strands of an ECM material woven with another ECM material or a structural reinforcing material such as ePTFE.

Another example of techniques to control remodelable retraction include coating of the remodelable material with a bioactive composition such as heparin or PTX. In one embodiment, the remodelable material is rendered non-thrombogenic by applying heparin to the lumen of the remodelable material. Heparin can be applied to the remodelable material, by a variety of well-known techniques. For illustration, heparin can be applied to the remodelable material in the following three ways. First, benzalkonium heparin (BA-Hep) isopropyl alcohol solution is applied to the prosthesis by applying the solution to the remodelable material or soaking the remodelable material in the solution, and then air-drying it. This procedure treats the remodelable material, such as collagen, with an ionically bound BA-Hep complex. Second, a suitable carbodiimide, such as a water-soluble carbodiimide, for example, N-ethyl-N'-(3-dimethylaminopropyl) carbodiimide hydrochloride (EDC) can be used to activate the heparin and then to covalently bond the heparin to the remodelable material, such as collagen fiber. Third, EDC can be used to activate the remodelable material, then covalently bond protamine to the remodelable material and then ionically bond heparin to the protamine. Many other coating, bonding, and attachment procedures are well known in the art which could also be used.

Another example includes treating the remodelable material with a crosslinking agent to at least partially crosslink the remodelable material. Cross-linking agents include glutaraldehyde, carbodiimide, and polyepoxy containing agents. Compared with other known methods, glutaraldehyde (GA) crosslinking of collagen provides materials with the highest degree of crosslinking. Glutaraldehyde is a five carbon aliphatic molecule with an aldehyde at each end of the chain rendering it bifunctional. The aldehyde is able to chemically interact with amino groups on collagen to form chemical bonds. This crosslinking agent is readily available, inexpensive, and forms aqueous solutions that can effectively crosslink tissue in a relatively short period. Using GA crosslinking, increased resistance to biodegradation and reduced antigenicity improved mechanical properties of collagen-based materials can be achieved.

Various types of crosslinking agents are known in the art and can be used such as ribose and other sugars, oxidative agents and dehydrothermal (DHT) methods. For instance, one crosslinking agent is 1-ethyl-3-(3-dimethylaminopropyl) carbodiimide hydrochloride (EDC). Alternatively, sulfo-N-hydroxysuccinimide is added to the EDC crosslinking agent as described by Staros, J. V., Biochem. 21, 3950-3955, 1982. Besides chemical crosslinking agents, the layers may be bonded together by other means such as with fibrin-based glues or medical grade adhesives such as polyurethane, vinyl acetate or polyepoxy. Other methods of crosslinking remodelable materials of the invention are disclosed, for example, in U.S. Pat. No. 6,117,979 to Hendricks et al. For instance, crosslinking can also be accomplished with diisocyanates by bridging of amine groups on two adjacent polypeptide chains. Another method of crosslinking involves the formation of an acyl azide. The acyl azide method involves the activation of carboxyl groups in the polypeptide chain. The activated groups form crosslinks by reaction with collagen amine groups of another chain. Alternatively, a method has recently been developed that does not need an esterification step or the use of hydrazine. In this method, a carboxyl group is converted to an acyl azide group in one single step by reaction with diphenylphosphorylazide (DPPA). Also, water-soluble carbodiimides can be used to activate the free carboxyl groups of glutamic and aspartic acid moieties in collagen. Yet another crosslinking method uses epoxy compounds to crosslink collagen. See, for example, U.S. Pat. No. 4,806,595 to Noishiki et al. and U.S. Pat. No. 5,080,670 to Imamura et al. One technique for regulating remodelable retraction includes layering remodelable materials or aligning collagen fibers in various ways in one or more layers of the remodelable material. In one embodiment, the method of U.S. Pat. No. 6,572,650 to Abraham et al. can be used to prepare layers of extracellular matrix remodelable material bonded together by dehydrating them while in wrapped arrangement on a sleeve-covered mandrel. While not wishing to be bound by theory, it is believed that dehydration brings the extracellular matrix components, such as collagen fibers, in the layers together when water is removed from the spaces between the fibers in the matrix.

Another technique for regulating remodelable retraction includes perforation of the remodelable material. In some embodiments, perforated sheets of extracellular matrix material can be used as a remodelable material, as disclosed in U.S. Pat. No. 6,379,710 to Badylak et al., which is incorporated herein by reference.

The remodelable material may also be treated with substances that enhance or exclude particular varieties of cellular or tissue ingrowth. These substances can influence the remodelable retraction process. Such substances include, for example, osteoinductive, angiogenic, mitogenic, or similar substances, such as transforming growth factors (TGFs), for example, TGF-alpha, TGF-beta-1, TGF-beta-2, TGF-beta-3; fibroblast growth factors (FGFs), for example, acidic and basic fibroblast growth factors (aFGF and bFGF); platelet-derived growth factors (PDGFs); platelet-derived endothelial cell growth factor (PD-ECGF); tumor necrosis factor alpha (TNF-alpha); tumor necrosis factor beta (TNF-b); epidermal growth factors (EGFs); connective tissue activated peptides (CTAPs); osteogenic factors, for example, BMP-1, BMP-2, BMP-3MP-4, BMP-5, BMP-6, BMP-7, BMP-8, BMP-9; insulin-like growth factor (IGF), for example, IGF-I and IGF-II; erythropoietin; heparin binding growth factor (hbgf); vascular endothelium growth factor (VEGF); hepatocyte growth factor (HGF); colony stimulating factor (CSF); macrophage-CSF (M-CSF); granulocyte/macrophage CSF (GM-CSF); nitric oxide synthase (NOS); nerve growth factor (NGF); muscle morphogenic factor (MMP); Inhibins (for example, Inhibin A, Inhibin B); growth differentiating factors (for example, GDF-1); Activins (for example, Activin A, Activin B, Activin AB); angiogenin; angiotensin; angiopoietin; angiotropin; antiangiogenic antithrombin (aaAT); atrial natriuretic factor (ANF); betacellulin; endostatin; endothelial cell-derived growth factor (ECDGF); endothelial cell growth factor (ECGF); endothelial cell growth inhibitor; endothelial monocyte activating polypeptide (EMAP); endothelial cell-viability maintaining factor; endothelin (ET); endothelioma derived mobility factor (EDMF); heart derived inhibitor of vascular cell proliferation; hematopoietic growth factors; erythropoietin (Epo); interferon (IFN); interleukins (IL); oncostatin M; placental growth factor (PlGF); somatostatin; thrombospondin; vasoactive intestinal peptide; and biologically active analogs, fragments, and derivatives of such growth factors. The remodelable material can also comprise mitogens to stimulate cell growth and/or differentiation, agents to stimulate cell migration to a site of injury within the body vessel, growth factors, and cells to restore or replace tissue.

In other embodiments, the remodelable material may comprise a therapeutic agent for treatment of vessel wounds, including, for example, anti-platelet agents such as aspirin and the like, anti-coagulant agents such as coumadin and the like, antibiotics, anti-thrombus deposition agents such as polyanionic polysaccharides including heparin, chondroitin sulfates, hyaluronic acid and the like, urokinase, streptokinase, plasminogin activators and the like, wound healing agents such as transforming growth factor beta (TGF beta) and the like, glycoproteins such as laminin, fibronectin and the like, and various types of collagens.

A remodelable material may also include a variety of other therapeutic agents, including passively functioning materials such as hyaluronic acid, as well as active agents such as growth hormones. A wide variety of therapeutic agents may be included in a remodelable material, including, for example, cells, proteins (including enzymes, growth factors, hormones and antibodies), peptides, organic synthetic molecules, inorganic compounds, natural extracts, nucleic acids (including genes, antisense nucleotides, ribozymes and triplex forming agents), lipids and steroids, carbohydrates (including heparin), glycoproteins, and combinations thereof.

The remodelable material may be treated in other ways to desirably affect the remodelable retraction of the body vessel wall, such as the extent, rate or location of remodelable retraction. One skilled in the art can also refer to other resources to provide such alternative treatments for remodelable materials. For example, U.S. Patent Application 2003/0175410 A1 of Campbell et al., published Sep. 18, 2003 and incorporated herein by reference, provides a variety of other treatments for remodelable materials that can influence remodeling properties. Textbooks such as "Basic & Clinical Pharmacology," 6th Ed., Bertram G. Katzung, Ed., Appleton & Lange (1995) and Joel G. Hardman et al., Eds., "Goodman & Gilman's The Pharmacological Basis of Therapeutics," 9th Ed., McGraw-Hill (1996) also provide various compounds that can be incorporated in the remodelable material to influence the remodelable contraction process.

Support Frame

In certain embodiments, the remodelable material can be optionally attached to a support frame. The support frame can be made from one or more suitable materials. Examples of suitable materials include, without limitation: stainless steel (such as 316 stainless steel), nickel titanium (NiTi) alloys (such as Nitinol) and other shape memory and/or superelastic materials, MP35N, gold, silver, a cobalt-chromium alloy, tantalum, platinum or platinum iridium, or other biocompatible metals and/or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhidride, polyether sulfone, polycarbonate, polypropylene, high molecular weight polyethylene, polytetrafluoroethylene, or other biocompatible polymeric material, or mixture of copolymers thereof, or stainless steel, polymers, and any suitable composite material.

In one embodiment, the frame is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. In certain embodiments, the frame is formed partially or completely of alloys such as nitinol (NiTi) which have superelastic (SE) characteristics. However, while some embodiments provide frames made from shape memory materials, other embodiments comprise other materials such as stainless steel, MP35N and other suitable materials. Some embodiments provide frames that are not self-expanding, or that do not comprise superelastic materials.

Preferably, the support frame does not prevent or substantially interfere with remodelable retraction of the interior wall of a body vessel. In one preferred embodiment, a support frame maintains the remodelable material in contact with the interior wall of a body vessel such as a vein, without substantially interfering with the remodelable retraction of the interior vessel wall.

The support frame can also optionally comprise, or be formed entirely from, a remodelable material attached to a compliant, low profile, biocompatible, hemocompatible or bioresorbable support frame. The support frame can be formed in any suitable shape, including a ring, a stent, a tube, or a zig-zag configuration. In one embodiment, the support frame can be self-expanding or balloon-expandable.

The support frame can be formed from a variety of medical grade polymers having properties that permit the frame to function as a supporting structure for the remodelable material. In some embodiments, the support frame comprises a bioabsorbable or remodelable material.

The support frame can comprise a bioabsorbable material that can be degraded and absorbed by the body over time to advantageously eliminate a frame structure from the vessel before, during or after the remodeling process. A number of bioabsorbable homopolymers, copolymers, or blends of bioabsorbable polymers are known in the medical arts. These include, but are not necessarily limited to, polyesters, poly (amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethlyene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

Some specific examples of bioabsorbable materials include poly(epsilon-caprolactone), poly(dimethyl glycolic acid), poly(hydroxy butyrate), poly(p-dioxanone), polydioxanone, PEO/PLA, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, collagen, hyaluronic acid, hydroxyethyl starch, and gelatin.

There are also a number of naturally derived bioabsorbable polymers that may be suitable, including modified polysaccharides such as cellulose, chitin, and dextran or modified proteins such as fibrin and casein.

Implantation of Remodelable Materials

Embodiments of the present invention provide remodelable materials within a body vessel to retract the interior walls of the body vessel. In some embodiments, the remodelable materials retract the body vessel to restore or improve the function of incompetent venous valves, for example by retracting the bases of two venous valve leaflets closer together to promote increased coaptation of the venous valve leaflets.

In some embodiments, the remodelable material is in contact with the wall of a body vessel upon implantation therein. The phrase "remodelable material in contact with the wall of a body vessel within a lumen of a body vessel" means that the remodelable material interacts with the vessel such that the retraction of the remodelable material during the remodeling process results in some retraction of at least a portion of the interior vessel wall. In some embodiments, the interior vessel wall can retract in response to the retraction of the remodelable material during remodeling. In some embodiments, portions of the remodelable material, or even an entire surface, can be physically touching the interior wall of a vessel. For example, in one embodiment, the invention can provide a remodelable material contacting the vessel wall through projections, such as barbs, that enter the wall of the vessel to anchor the remodelable material and serve to retract the vessel wall during remodeling.

Preferably, in some embodiments, the remodelable material is deployed at a distance from the base of a leaflet of an incompetent venous valve. Preferably, the distance is a "treatment effective distance," which is a distance between the remodelable material and the base of a leaflet of a venous valve that is effective to remodelably retract the leaflet inward within the lumen of the body vessel. Distances in accordance with the present invention are preferably measured along the body vessel. For example, for treating venous valve insufficiency by implanting a remodelable material at a site within the lumen of a body vessel, the distance from the base of a leaflet of an incompetent venous valve to the site of implantation should be one that is selected to provide the desired amount of retraction of the body vessel wall. In a preferred embodiment, the remodelable material implanted at a treatment effective distance induces remodelable retraction of the interior wall of a body vessel that pulls at least one venous valve leaflet toward the center of the lumen during the remodeling process. Examples of a treatment effective distance include 1, 2, 3, 4, 5, 6, 7, 8, 9, 10, 11, 12, 13, 14, 15, 16, 17, 18, 19, 20, 25, 30, 35, 40, 45 and 50 mm from the base of a valve leaflet, as well as 3, 4, 5, 6, 7, 8, 9, 10, 20, 30, 40, and 50 cm from the base of a valve leaflet.

In one preferred embodiment, the treatment effective distance is between a placement adjacent to the base of a venous valve leaflet and 50 mm in either direction from this point. In a more preferred embodiment, the treatment effective distance is between about 30 mm from the base of a venous valve leaflet and adjacent to the base of the venous valve leaflet. In another preferred embodiment, the treatment effective distance is between about 15-25 mm from the base of a venous valve leaflet and adjacent to the venous valve leaflet. For example, the treatment effective distance can be 15, 16, 17, 18, 19, 20, 21, 22, 23, 24, or 25 mm from the base of a venous valve leaflet, as measured along the interior of the vein.

Various imaging methods including ultrasound, x-rays, fluoroscope, magnetic resonance imaging, and the like can be employed to monitor location or orientation of remodelable material, or measure distances moved by a remodelable material or an associated support structure or delivery system within the lumen of a body vessel.

Distances along a body vessel, for example with respect to a venous valve, can be measured by any suitable method. The catheter delivery system can comprise a means for measuring distances along a body vessel, such as indicia, radiopaque markers on the delivery catheter or on a support frame attached to the remodelable material, or transmission of a signal correlated to the location, displacement or orientation of a remodelable material for deployment within the body vessel. For example, translation of at least a portion of the delivery system can correlate to the movement of a remodelable material at the proximal end of a catheter within the body vessel. Location of venous valves or sphincters in body vessels can be ascertained by methods known in the art. Three non-limiting exemplary ways to monitor location of venous valves or remodelable material within a body vessel include: (1) correlating movement of the proximal end of a catheter to patient anatomy, (2) imaging a portion of a vein, a remodelable material or associated support structure or delivery device, or (3) sensing resistance to translation of the proximal end of the catheter.

In one embodiment, an implanted remodelable material or an associated support frame or delivery system can include a marker to verify the location of the remodelable material during and after implantation. For example, the remodelable material, the support frame, the delivery device, or any combination thereof, can comprise a marker material, such as a radiopaque portion of the frame that would be seen by remote imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film.

In another embodiment, the remodelable material can be attached to a support that provides a traceable signal that can be monitored to provide information about the location, orientation and movement of the remodelable material. Numerous other methods can be employed to measure the location, movement, distance moved, and orientation of the remodelable material within a body lumen, as known in the art.

Various types and configurations of remodelable materials can be implanted within a body vessel according to certain embodiments of the invention. For example, the remodelable materials used with various embodiments of the invention can be formed into various shapes, stacked in layers, or treated with various substances to control the amount and time of retraction of the vessel wall. In some embodiments, the remodelable material can be attached to a support frame.

Figure 4:
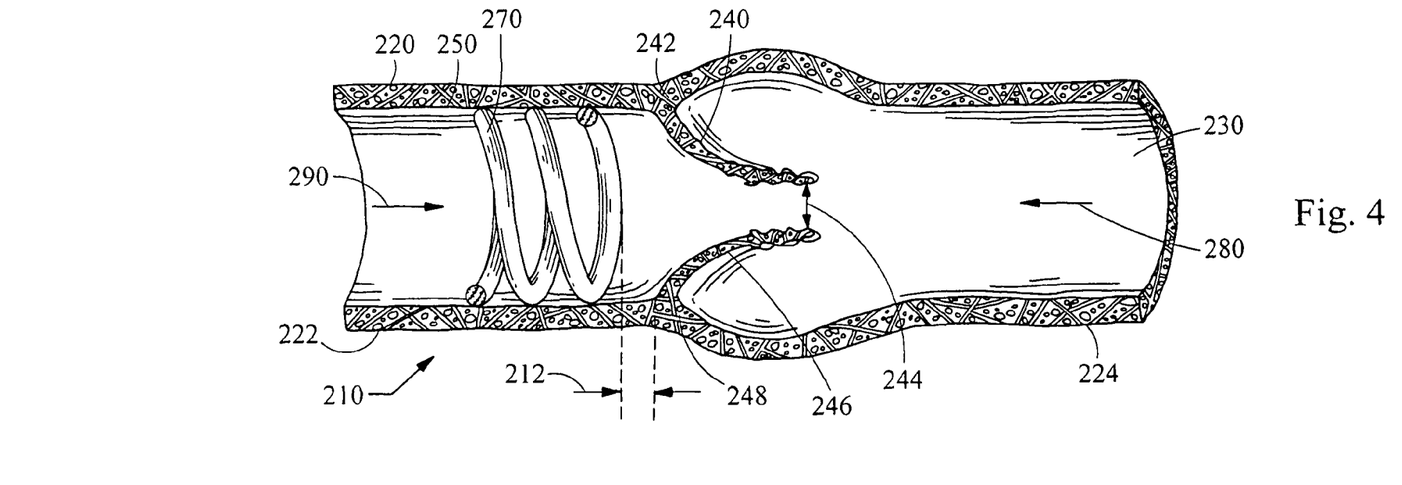
FIG. 4 provides a cut-away view of an embodiment of the invention comprising implantation of a helical remodelable material within a body vessel at a distance from an incompetent venous valve.

In certain embodiments, the remodelable material can be implanted within a vessel in any suitable configuration, such as a tube, a coil, a ring shape, a helix, or a zig-zag configuration. For example, in FIG. 4, a helical coil of a remodelable material 270 is deployed within the lumen 230 of a body vein 220, at a treatment effective distance 212 upstream from the base 242 of a first leaflet 240 and the base 248 of a second leaflet 246 of an incompetent venous valve 210. In the illustrated embodiment of FIG. 4, the outside of the coil of remodelable material 270 is fixedly attached to the interior wall 250 of the body vessel 220. During remodeling of the helical coil of remodelable material 270, the interior wall 250 of the body vessel 220 will gradually retract toward the center of the lumen 230, so as to draw the base 242 of the first leaflet 240 closer to the base 248 of the second leaflet 246. The contraction of the vessel wall during the remodeling process will draw the leaflets into greater coaptation and decrease the amount of retrograde flow 280 while allowing fluid flow 290 in the opposite direction.

Figure 5:
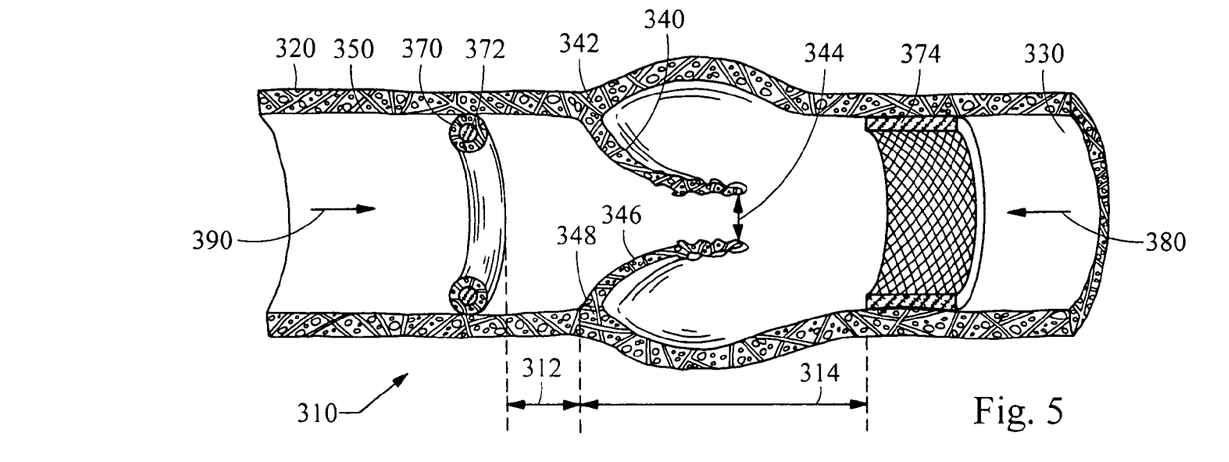
FIG. 5 provides a cut-away view of another embodiment of the invention comprising implantation of two remodelable material implants within a body vessel, each at distances from an incompetent venous valve.

FIG. 5 illustrates another embodiment, where remodelable material is implanted both upstream from and downstream from a native incompetent venous valve 310. A first remodelable material implanted upstream from the incompetent venous valve 310 is a tubular ring of remodelable material 370 enclosing a bioabsorbable support ring 372. The first remodelable material tubular ring 370 and ring support 372 are positioned at a first treatment effective distance 312 from the base 342 of the first leaflet 340 and the base 348 of the second leaflet 346. A second remodelable material is an annular ring 374 comprising two layers of remodelable material made from aligned collagen fibers oriented to optimize retraction of the vessel wall to improve venous valve competency. The second remodelable material ring 374 is positioned at a second treatment effective distance 314 downstream from the leaflet base. Both remodelable materials are placed in contact with the interior wall 350 of the lumen 330 of a body vessel 320. As remodeling processes occur after implantation of the remodelable materials, the interior wall 350 will contract, thereby drawing the first leaflet 340 and the second leaflet 346 into greater coaptation at the ends distal to the leaflet bases. As the interior wall 350 of the vessel remodelably contracts, the base 342 of the first leaflet 340 and the base 348 of the second leaflet 346 will both be drawn toward the center of the lumen 330, thereby closing the gap 344 between the free edges of the leaflets, distal to each leaflet base, when the venous valve is subject to retrograde fluid flow 380, but still allowing fluid flow 390 in an opposite direction.

In some embodiments, the remodelable material can be retained within the body vessel by a variety of methods known in the art. In one embodiment, the remodelable material is attached to a support frame that is retained within the body vessel by pressure against the vein wall exerted by the frame. In another embodiment, the remodelable material is secured and retained in the body vessel by barbs on the frame or remodelable material that engage the vessel wall. For example, the support frame of the remodelable material itself can include integral barbs that extend from the frame. For instance, barbs can be formed by V-shaped cuts transversing the thickness of a flat metal frame, which are bent outward to form the barb. In some embodiments, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used. In some embodiments, the barbs or any portion of an implantable material or support frame can comprise a radiopaque or other marker material that can be remotely imaged, for example using x-rays, Magnetic Resonance Imaging, ultrasound or any other suitable imaging methods. Other modifications of the surface of the remodelable material can be used to secure and retain the remodelable material, such as holes in a layer of remodelable material that allow greater adhesion to the wall of the vein upon implantation therein.

Preferably, the remodelable material is implanted and retained within the lumen of a body vessel for a retraction-effective period of time. The phrase "retraction-effective period of time" refers to a period of time during which remodelable retraction can or does occur. Remodelable retraction can occur before, during or after remodeling processes, such as cellular migration or cell-mediated contraction occur in a remodelable material. In some embodiments, a retraction-effective period of time refers to the time during which remodeling processes are occurring.

While not discussed to limit the scope of the invention by theory, recent investigations of remodeling of SIS within animal body vessels can provide guidance for determining a retraction-effective period of time. As discussed below, based on some investigations, the remodeling process appears to begin within about 2 days, or possibly even within moments, after implantation of SIS. Similarly, a number of investigations (discussed below) show that SIS remodeling has been observed on a time scale of about a week to three months in different studies.

In one investigation, researchers implanted a small caliber vascular graft from porcine small intestine submucosa in a canine carotid artery and compared the remodeling process with an autogenous saphenous vein graft implanted in the contralateral carotid artery. At 2 days after implant, the luminal surface of the SIS graft was covered with a thin (30 µm) fibrin meshwork. Smooth muscle cells were observed in the new intima (fibrin meshwork) by 28 days. By 90 days, both types of graft had arterialized with an intima covered by endothelium, a smooth muscle media and marked adventitial fibrosis. Similar histology was observed at 180 days. Sandusky et al., "Histologic findings after in vivo placement of small intestine submucosal vascular grafts and saphenous vein grafts in carotid artery in dogs," Am. J. Pathol., 140(2), 317-24 (Februray 1992).

In another investigation, SIS venous conduit was implanted between the portal vein and inferior vena cava in Lewis rats. Smooth luminal surface with endothelial-like cells were observed on the implanted SIS material by 3 weeks. Subsequent histology of excised SIS venous grafts demonstrated a confluent luminal endothelial monolayer, absence of thrombus, and neovascularization in the SIS graft. Kim et al., "Small intestinal submucosa as a small-caliber venous graft: a novel model for hepatocyte transplantation on synthetic biodegradable polymer scaffolds with direct access to the portal venous system," J. Pediatr. Surg., 34(1), 124-128 (January 1999).

Another study found that SIS vascular grafts explanted after about 60-days were found to be encased in fibrous tissue. Measurements of mechanical properties (compliance, elastic modulus and burst pressure) of the explanted remodeled grafts approached the mechanical properties of the original vessel, indicating that remodeled tissue on the SIS graft possessed similar mechanical properties. Roeder et al., "Mechanical remodeling of small-intestine submucosa small-diameter vascular grafts—a preliminary report," Biomed. Instrum. Technol., 35(2), 110-120 (March 2001).

A study of SIS implanted in the abdominal wall of dogs and rats over a 2 year period indicated that SIS material appeared fully remodeled by 3 months. After 3 months, the SIS was no longer recognizable and appeared to be replaced by host tissue, including collagenous connective tissue, adipose tissue and bundles of skeletal muscle. Notably, SIS was observed to serve as a scaffold for new skeletal muscle tissue in this study. Badylak et al., "Morphologic Study of Small Intestinal Submucosa as a Body Wall Repair Device," J. Surg. Research, 103, 190-202 (April 2002).

A recent study of square stent-based bicuspid venous valves comprising small intestinal submucosa implanted in the venae cavae of adult sheep for 5 weeks showed remodeling of the SIS material. Remodeling was indicated by the presence of newly formed collagen fibers on the SIS, fibroblasts and inflammatory cells penetrating the SIS leaflets, endothelial cells on the surface of the SIS, and neovascularization of the SIS material. Endothelial cells were found on both surfaces of the SIS valve leaflets. Researchers concluded that the SIS-based valve remodeling occurred independently of vessel wall contact by recruitment of cells directly from circulation. Brountzos, et al., "Remodeling of suspended small intestinal submucosa venous valve: an experimental study in sheep to assess the host cells' origin," J. Vasc. Interv. Radiol., 14(3), 349-356 (March 2003).

The rate of remodelable retraction of the body vessel can depend on a variety of factors, including, for example, the exact composition and configuration of the remodelable material. In some embodiments, the wall of a body vessel can be substantially retracted in less than about 1 year, 9 months, 6 months, 4 months, 3 months, 2 months, 6 weeks, or 1 month.

In some embodiments, the remodelable retraction can begin occurring within 1 minute, 1 hour, or 1, 2, 3, 4, 5, 6, 7 days or more. Preferably, remodelable retraction can begin within about 2 days and substantial remodelable retraction can occur within about 6 months. "Substantial retraction" refers qualitatively to a state in the body vessel where remodeling is substantially completed and the continued rate of remodelable retraction is negligible.

Delivery of Remodelable Material

A variety of delivery systems are suitable for deploying the remodelable material within a body vessel. In some embodiments, the delivery systems for remodelable materials are generally comprised of catheters with the remodelable material axially surrounding a portion of the distal end of the catheter. In one embodiment, the profile of the catheter is minimized. A remodelable material may also be implanted using a laparoscope or thoracoscope to any intraperitoneal or extraperitoneal or thoracic organ. For example, a remodelable material could implanted in the region of the gastroesophageal junction for the correcting of gastroesophageal reflux. This could be performed either with a thoracoscope implanting the remodelable material in the esophageal portion of the gastroesophageal region, or via a laparoscope by implanting the remodelable material in the gastric portion of the gastroesophageal region, or by a combined approach.

Figure 6:
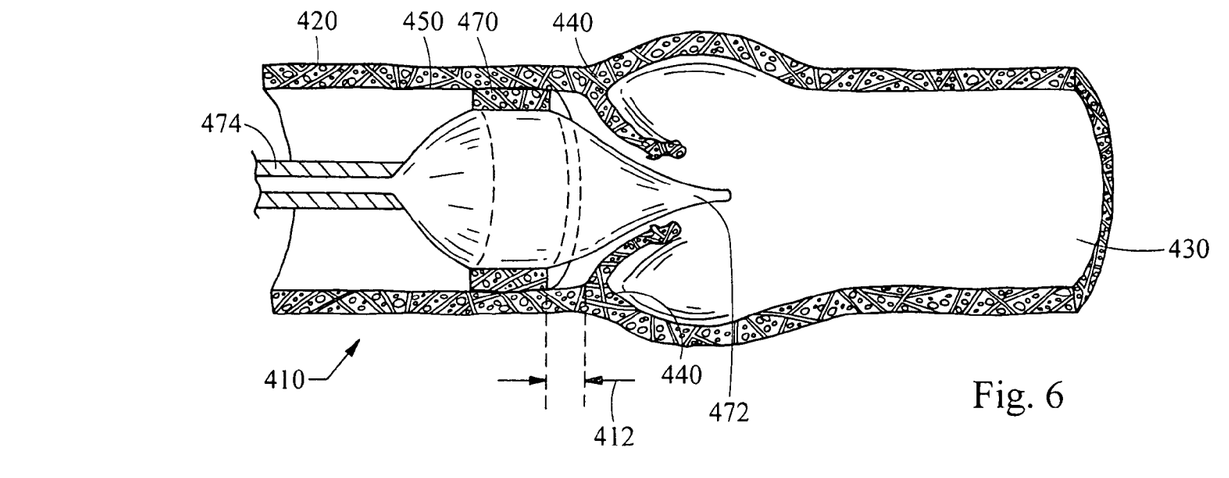
FIG. 6 provides a cut-away view illustrating intraluminal deployment of remodelable material by expanding a balloon.

In one embodiment, the remodelable material can be delivered to a point of treatment within the lumen of a body vessel using an expandable element, for example a balloon, an expandable "basket" frame or loop, or a malecot. For example, FIG. 6 illustrates one embodiment of the invention, where a ring-shaped remodelable material 470 is deployed at a treatment effective distance 412 from the base 440 of an incompetent venous valve 410 by an inflatable balloon 472 at the distal end of a catheter 474 delivery system. The inflation of the balloon 472 presses the remodelable material 470 against the interior wall 450 within the lumen 430 of a body vessel 420. In some embodiments, a balloon-expandable support frame can be implanted with a remodelable material. For example, a catheter having a remodelable material disposed annularly around an inflatable portion can be delivered to a desired location within a body passageway, where the inflatable portion is expanded to deploy the remodelable material within the vessel. Fluoroscopy, and or other conventional techniques may be utilized to insure that the catheter and remodelable material, optionally including a support frame, are delivered to the desired location. In one embodiment, the remodelable material can be attached to a support frame that is then controllably expanded and deformed by controllably expanding the expandable inflatable portion of catheter, typically a balloon. In this embodiment, the support frame and remodelable material can deformed by the balloon expansion radially outwardly to bring the remodelable material into contact with the walls of the body passageway. In this regard, the expandable inflatable portion of the catheter may be a conventional angioplasty balloon as is already known in the art. According to this embodiment, after the desired expansion and deformation of the remodelable material or support frame associated therewith has been accomplished, the angioplasty balloon may be deflated and the catheter removed in a conventional manner from the passageway.

The remodelable material can be secured to an expandable element by any suitable means. For example, a temporary adhesive can be applied to the expandable element. In one embodiment, a balloon expandable element can be pleated with the remodelable material to retain the remodelable material between the pleats in the compressed state. Any form of temporary retaining means may be used to maintain the remodelable material in association with the expandable element prior to deployment of the remodelable material. For example, other mechanical, chemical or other physical retaining interactions between the remodelable material and the expanding element may be used.

Figure 7:
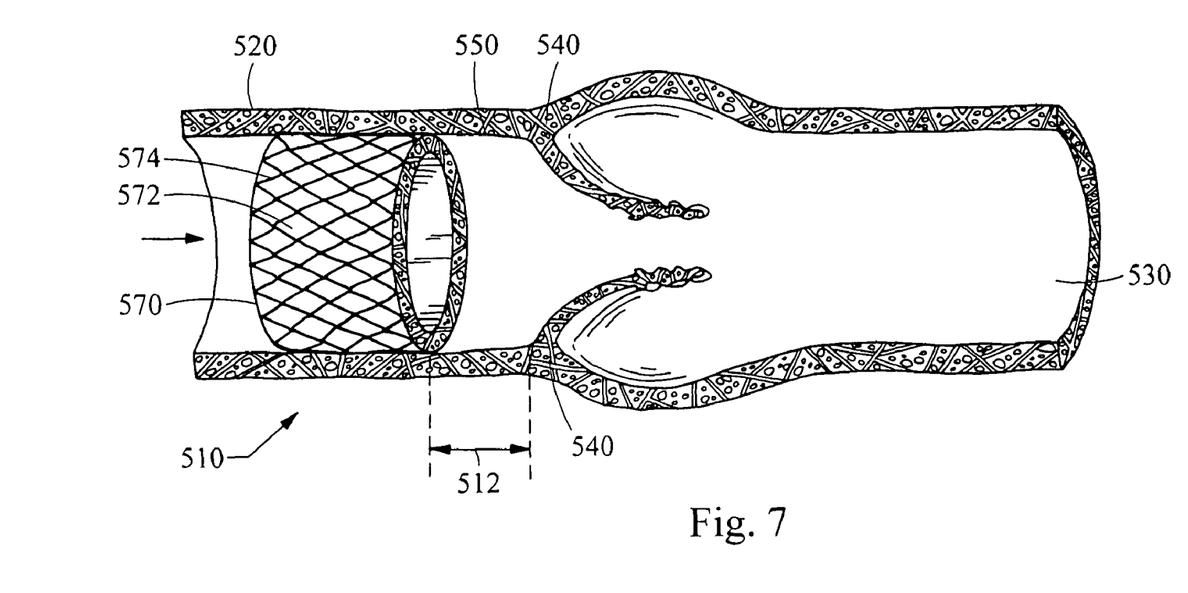
FIG. 7 provides a cut-away view illustrating intraluminal deployment of remodelable material by expanding a self-expanding support frame.

In another embodiment, the remodelable material can be attached to a self-expanding frame. For example, FIG. 7 illustrates an embodiment of the invention, where a tube-shaped implant 570 comprising a self-expanding support frame 574 inside a remodelable material sleeve 572. Preferably, the support frame 574 can be formed at least in part from a bioabsorbable material, although this is not required. The remodelable material is held against the interior wall 550 of the lumen 530 of a body vessel 520 at a treatment effective distance 512 from the base 540 of an incompetent venous valve 510.

Accordingly, in some embodiments, the remodelable material can be confined in a reduced radius for delivery to the deployment site. Once the remodelable material is deployed, the catheter is removed, leaving the remodelable material implanted at the desired location in contact with the vessel wall. In some embodiments, the remodelable material is attached to a support structure, which can be delivered in a compressed geometry at or near the distal end of a catheter delivery and deployed at or near the site of implantation of the remodelable material.

Figure 8A:
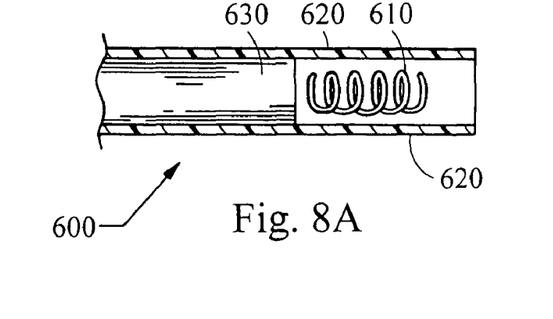
FIG. 8A and FIG. 8B provide cut-away views illustrating two delivery systems useful for delivering a remodelable material to a point of treatment within a body vessel.
Figure 8B:
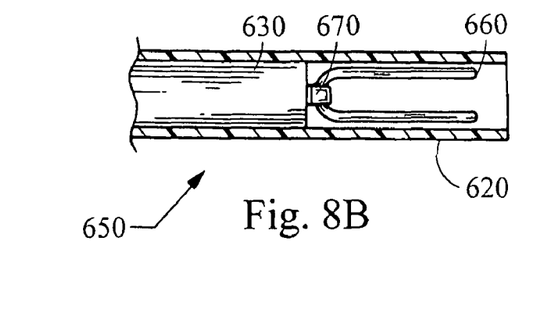

A variety of techniques can be used for holding a remodelable material, with or without an associated support structure, in a compressed delivery configuration while moving the distal end of the catheter to the deployment site. FIG. 8A and FIG. 8B illustrate two examples of delivery systems for protectively retaining a remodelable material while delivering the remodelable material intraluminally through a body vessel to a point of treatment. In FIG. 8A, the system 600 comprises a helical remodelable material 610, within a cavity defined by a protective sheath 620 that encloses the remodelable material during the delivery process. Also provided is a pusher 630 member positioned to translate the remodelable material 610 out of the sheath 620 and into the lumen of a body vessel at the point of treatment. In FIG. 8B, a second system 650 provides a retention mechanism 670 on the distal end of the pusher 630 to retain a horse-shoe shaped remodelable material 660 within a protective sheath 620 during delivery to a point of treatment. The retention mechanism shown in FIG. 8B is a clip, although any mechanical retention mechanism can be used. In one embodiment, instead of a retention clip, gripping members at the end of the delivery catheter can retain the remodelable material in a reduced radius delivery configuration prior to implantation. Another common technique for maintaining the remodelable material, optionally including an associated support frame, in a reduced radius delivery configuration is using a sheath which surrounds the remodelable material and compresses it around the catheter. This technique is disclosed for stents, but can be adapted for use with remodelable material. For example, U.S. Pat. No. 5,071,407 (Termin) and U.S. Pat. No. 5,064,435 (Porter), both disclose a silicon rubber sheath to compress the stent. A similar technique is disclosed in U.S. Pat. No. 5,026,377 (Burton) and U.S. Pat. No. 5,078,720 (Burton). One variation on surrounding the remodelable material with a sheath is disclosed in U.S. Pat. No. 4,732,152 (Wallsten); U.S. Pat. No. 4,848,343 (Wallsten) and U.S. Pat. No. 4,875,480 (Imbert), all of which are incorporated herein by reference.

Methods of Treatment

"Symptoms of venous valve insufficiency" refers to any symptom, including a sensation or change in body function that can be diagnostically associated with venous valve insufficiency in the subject. The subject can be animal or human.

The present invention also provides for methods of deploying a remodelable material within a body vessel. A remodelable material can be deployed in various body vessels to treat a variety of conditions, including: venous valve insufficiency, gastroesophageal reflux disease, urinary and rectal incontinence, dysphonia, and the reconstruction of body vessels.

In one embodiment, a remodelable material can be implanted to improve venous valve function. One method comprises the step of inserting a remodelable material into a body vessel. For example, a delivery system can be employed to advance a delivery system comprising a remodelable material to a first point of treatment. Preferably, this step comprises advancing a delivery system that includes a sheath, a remodelable material device and an interior guide wire sheath through a body vessel. Alternatively, this step can comprise advancing a remodelable material through a sheath that has previously been inserted into the body vessel.

In cases of acid reflux, remodelable materials may be used to treat a deficiency of the pyloric sphincter. Gastroesophageal reflux disease (GERD) involves the regurgitation of stomach gastric acid and other contents into the esophagus or diaphragm. Atypical manifestations of GERD include: asthma; chronic cough; laryngitis; sore throat; and non-cardiac related chest pain. GERD can be treated by implanting a remodelable material adjacent to the lower esophageal sphincter.

In addition to its use for the endoscopic treatment of reflux, implantation of remodelable material may also be applicable for the treatment of other medical conditions, such as urinary and rectal incontinence, dysphonia, reconstruction of portions of body vessels or sphincter muscles. The remodelable material can also be implanted near a deficient sphincter muscle for the treatment of vesico-ureteral reflux or urinary incontinence. Remodelable material can implanted to treat urinary incontinence and/or vesicoureteral reflux by reforming or repairing tissue (e.g., sphincter structures) within the urethra, ureters, and esophagus, thus causing a retraction and reduction in size of abnormally wide and loose lumens. These methods involve placement (e.g., implantation) of remodelable materials into the regions within or near the urethra, ureters, or esophagus.

At the point of treatment, the remodelable material can be deployed. The manner in which this step is accomplished will depend on the arrangement of the remodelable material within the delivery system. For example, if the remodelable material device is disposed annularly around an interior guide wire conduit, the remodelable material can be deployed by withdrawing the external sheath to expose the remodelable material and allow self-expansion of the remodelable material, or a support frame attached to the remodelable material, to occur. In other embodiments, the remodelable material can be contained within a lumen of an external sheath previously inserted into a body vessel and pushed in its compressed configuration to a point of treatment. At the point of treatment, the remodelable material can be deployed simply by forcing the medical device out of an end of a lumen.

The present invention also provides a method of supplying remodelable material for use in methods of treating human or veterinary patients in which it is desirable to deploy multiple intraluminal medical devices in a body vessel, for example in conjunction with procedures using the remodelable material to retract the interior walls of a body vessel.

Kits

Kits comprising a remodelable material are also provided, including kits further comprising a delivery system.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

The recitations of "embodiments," "one embodiment," "some embodiments," "other embodiments," "illustrative embodiments," "selected embodiments," "certain embodiments," and "another embodiment" herein are synonymous. All of these recitations refer to illustrative embodiments and are not exclusive of each other or of other embodiments not recited herein. Accordingly, the invention also provides embodiments that comprise combinations of one or more of the illustrative embodiments described above.

All references cited herein are hereby incorporated into this disclosure in their entirety.

We claim:

1. A method for remodelably retracting the interior wall of a body vessel by inducing contraction of a remodelable extracellular matrix material during a remodeling process on the interior wall of the body vessel, the method comprising:
    (a) inserting a delivery system including a remodelable extracellular matrix material without a support frame annularly disposed around a portion of a catheter into a vein, wherein the remodelable extracellular matrix material is isolated from a tissue source and has an implantable first size;
    (b) advancing the delivery system to a point of treatment within the vein;
    (c) implanting the remodelable extracellular matrix material in contact with an interior wall of a body vessel at the point of treatment within the vein to induce inward retraction of the body vessel wall with said inward retraction beginning only after said implanting of the remodelable extracellular matrix material and only upon remodeling of the remodelable extracellular matrix material, the point of treatment being in the superficial venous system or the deep venous system at a treatment-effective distance of up to about 50 mm from a base of a valve leaflet within the vein to remodelably retract the interior wall of the vein at the base of the valve leaflet radially toward the center of the lumen of the body vessel, and
    (d) maintaining the remodelable extracellular matrix material in contact with the interior wall of the body vessel for a time sufficient for the remodelable extracellular matrix material to undergo contraction after said implanting and during remodeling by patient tissue such that the size of the remodelable extracellular matrix material is reduced relative to its implantable first size, wherein said contraction during remodeling is effective after said implanting to pull a portion of the body vessel radially inward within the lumen of the body vessel to reduce the volume of the body vessel lumen at the point of treatment.

2. The method of claim 1, where the remodelable material comprises an extracellular matrix material having a thickness of about 100 to 200 micrometers.

3. The method of claim 1, where the remodelable material comprises at least two extracellular matrix materials, including an autologous tissue.

4. The method of claim 1, where the remodelable material comprises two or more layers of extracellular matrix material, including at least one cross-linked layer.

5. The method of claim 1, where the remodelable material comprises an Elastin or an elastin-like peptide.

6. The method of claim 1, where the remodelable material is perforated and comprises SIS.

7. The method of claim 6, where implanting the remodelable material further comprises the steps of:
inserting the remodelable material without a support frame into the lumen of a vein of the superficial venous system or the deep venous system containing a venous valve;
advancing the remodelable material to a point of treatment within the vein that is a distance of up to about 50 mm from the venous valve, as measured along the interior wall of the vein;
positioning the remodelable material in contact with an interior wall of the vein at the point of treatment; and
removing the catheter from the body vessel while maintaining the remodelable material in contact with the interior wall of the vein at the point of treatment.

8. The method of claim 1, where the remodelable extracellular matrix material is a first remodelable extracellular matrix material that is implanted at a first distance upstream from the base of the venous valve; the method further comprising the step of: implanting a second remodelable extracellular matrix material within the lumen of the body vessel at a second distance downstream from the base of the venous valve, such that the first remodelable extracellular matrix material and the second remodelable extracellular matrix material are maintained in contact with the wall of a body vessel without a support frame.

9. The method of claim 8, wherein the first remodelable material is implanted upstream from a native venous valve and the second remodelable material is implanted downstream from a native venous valve.

10. The method of claim 1, where the remodelable material has a thickness of about 100 to 200 micrometers and is implanted at a treatment-effective distance of between about 1 mm-about 50 mm from the base of a leaflet of the venous valve, as measured along the interior wall of the body vessel.

11. The method of claim 1, where the remodelable material is perforated.

12. The method of claim 1, where the body vessel is a vein and the remodelable material is implanted about 1-10 mm from the base of a leaflet of a venous valve within the vein, as measured along the interior wall of the vein.

13. The method of claim 1, further comprising the step of contacting the remodelable material with a crosslinking agent before implanting the remodelable material within the body vessel.

14. The method of claim 1, where the remodelable material is characterized by at least one of the following:
(a) the remodelable material is a multilaminate construct including a xenogenic biomaterial and an autologous material;
(b) the remodelable material comprises an Elastin or an elastin-like peptide; and
(c) the remodelable material comprises small intestine submucosa.

15. The method of claim 1, where the remodelable material is a multilaminate construct including a xenogenic biomaterial and an autologous material.

16. A method for treating venous valve insufficiency by remodelably retracting the bases of two venous valve leaflets closer together to promote increased coaptation of the venous valve leaflets of a native incompetent venous valve within a vein by inducing contraction of a remodelable material in contact with an interior wall of the vein, the method comprising:
(a) inserting a first remodelable material and a second remodelable material each annularly disposed without a support frame around an inflatable portion of a balloon catheter into a vein, where the first remodelable material and the second remodelable material are independently selected from the group consisting of: submucosa, renal capsule membrane, dura mater, pericardium, serosa, peritoneum membrane and basement membrane, and wherein the first remodelable material and the second remodelable material are isolated from a tissue source and each have an implantable first size;
(b) advancing the first remodelable material and the inflatable portion of the balloon catheter to a first point of treatment within the vein;
(c) first securing the first remodelable material to an interior wall of the vein at the first point of treatment by inflating the inflatable portion of the balloon catheter;
(d) deflating the inflatable portion of the balloon catheter and advancing the second remodelable material to a second point of treatment within the vein;
(e) second securing the second remodelable material to the interior wall of the vein at the second point of treatment, the first point of treatment and the second point of treatment each being in a body vessel of the superficial venous system or the deep venous system containing a venous valve including a leaflet having a base attached to the body vessel, the first point of treatment and the second point of treatment both being at a distance of up to about 50 mm from the base of the leaflet of the venous valve within the body vessel to induce remodelable retraction of the base of the leaflet radially inward toward the interior of the body vessel; and
(f) maintaining the first and second remodelable materials in contact with the interior wall of the body vessel for a time sufficient for the first and second remodelable materials to undergo contraction only upon remodeling by patient tissue such that the size of the first and second remodelable materials is reduced relative to their implantable first size only after said first and second securing steps, wherein said contraction during remodeling is effective to pull a portion of the body vessel radially inward within the lumen of the body vessel to reduce the volume of the body vessel lumen at the point of treatment.

17. The method of claim 16, where the first remodelable material and the second remodelable material are both maintained in contact with an interior wall of the body vessel for at least about 2 days.

18. The method of claim 16, where the first remodelable material comprises a crosslinked extra-cellular matrix material and has a thickness of about 100 to 200 micrometers.

19. The method of claim 16, where the first remodelable material and the second remodelable material comprises one or more materials independently selected from the group consisting of: an autologous tissue, elastin, an elastin-like peptide and SIS.

20. A method for retracting the interior wall of a vein, the method comprising:
(a) inserting a delivery system including a remodelable extracellular matrix material without a support frame into a vein, wherein the remodelable extracellular matrix material is isolated from a tissue source and has an implantable first size;

(b) advancing the remodelable extracellular matrix material to a point of treatment within the vein;
(c) implanting the remodelable extracellular matrix material in contact with an interior wall of a body vessel at the point of treatment within the vein, the point of treatment being in the superficial venous system or the deep venous system at a treatment-effective distance of up to about 50 mm from a base of a valve leaflet within the vein to retract the interior wall of the vein at the base of the valve leaflet radially toward the center of the lumen of the body vessel only after said implanting and only upon remodeling of the remodelable extracellular matrix material by patient tissue, and
(d) maintaining the remodelable extracellular matrix material in contact with the interior wall of the body vessel for a time sufficient for the remodelable extracellular matrix material to undergo contraction after said implanting and during remodeling by patient tissue such that the size of the remodelable extracellular matrix material is reduced relative to its implantable first size after said implanting and during remodeling by patient tissue, wherein said contraction during remodeling is effective after said implanting to pull a portion of the body vessel radially inward within the lumen of the body vessel to reduce the volume of the body vessel lumen at the point of treatment.

* * * * *